United States Patent [19]

Müller et al.

[11] Patent Number: 6,114,341
[45] Date of Patent: *Sep. 5, 2000

[54] PYRIMIDO[1,2-A]INDOLES

[75] Inventors: Ulrich Müller, Wuppertal; Peter Eckenberg, Erkrath; Rudi Grützmann, Solingen; Hilmar Bischoff; Dirk Denzer, both of Wuppertal; Stefan Wohlfeil, Hilden, all of Germany; Stefan Lohmer, Milan, Italy; Ulrich Nielsch; Peter Kolkhof, both of Wuppertal, Germany

[73] Assignee: Bayer Aktiengesellschaft, Leverkusen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/829,015

[22] Filed: Mar. 31, 1997

[30] Foreign Application Priority Data

Apr. 4, 1996 [DE] Germany .......................... 196 13 550

[51] Int. Cl.⁷ .......................... A01N 43/54; C07D 239/00
[52] U.S. Cl. .......................... 514/267; 544/252
[58] Field of Search .......................... 514/267; 544/252

[56] References Cited

U.S. PATENT DOCUMENTS

| | | | |
|---|---|---|---|
| 3,850,957 | 11/1974 | White | 260/309.6 |
| 4,783,455 | 11/1988 | Cliffe | 514/220 |
| 5,306,820 | 4/1994 | Decker et al. | 546/153 |
| 5,352,687 | 10/1994 | Muller et al. | 514/341 |
| 5,420,149 | 5/1995 | Müller et al. | 514/399 |
| 5,521,206 | 5/1996 | Müller et al. | 514/400 |
| 5,527,809 | 6/1996 | Müller-Gliemann et al. | 514/303 |
| 5,576,342 | 11/1996 | Müller | 514/399 |
| 5,705,498 | 1/1998 | Gaster et al. | 514/214 |

FOREIGN PATENT DOCUMENTS

| | | |
|---|---|---|
| 509359 | 10/1992 | European Pat. Off. . |
| 0513533 A2 | 11/1992 | European Pat. Off. . |
| 513533 | 11/1992 | European Pat. Off. . |
| 560163 | 9/1993 | European Pat. Off. . |
| 0622358 A1 | 11/1994 | European Pat. Off. . |
| 2200584 | 7/1972 | Germany . |
| 4302956 | 8/1994 | Germany . |
| 4309968 | 9/1994 | Germany . |

OTHER PUBLICATIONS

R.A. Glennon und M. von Stradtmann, J. Heterocycl. Chem. vol. 12, pp. 135–138, (1975).

C.A. Grob und O. Weissbach, Helv. Chim. Acta 44, pp. 1748–1753, (1961).

A.N. Kost, R.S. Sagitullin, V.I. Gorbunov und N. N. Modyanov, Khim. Geterosikl. Soedin vol. 6, 359–363, (1970); English translation pp. 334–337.

*Primary Examiner*—Mukund J. Shah
*Assistant Examiner*—Tamthom T. Ngo
*Attorney, Agent, or Firm*—Norris, McLaughlin & Marcus, P.A.

[57] ABSTRACT

The pyrimido[1,2-a]indoles according to the invention are prepared by reacting appropriately substituted phenylacetic acid derivatives with phenylglycinols. The pyrimido[1,2-a] indoles can be used as active compounds in medicaments, in particular in medicaments with antiatherosclerotic activity.

18 Claims, No Drawings

PYRIMIDO[1,2-A]INDOLES

The present invention relates to pyrimido[1,2-a]indoles, to processes for their preparation and to their use as medicaments, in particular as antiatherosclerotic medicaments.

It is known that elevated blood levels of triglycerides (hypeitriglyceridaemia) and cholesterol (hypercholesterolaemia) are associated with the development of atherosclerotic changes in vessel walls and coronary heart disease.

There is, furthermore, a distinctly increased risk of developing coronary heart disease when these two risk factors occur in combination, which is in turn associated with an overproduction of apolipoprotein B-100. Hence there is a continuing pressing need to provide effective medicaments for controlling atherosclerosis and coronary heart disease.

The present invention relates to pyrimido[1,2-a]indoles of the general formula (I)

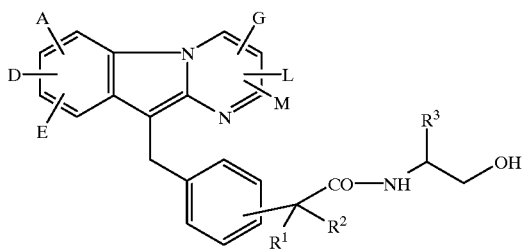

(I)

in which
- A, D, E, G, L and M are identical or different and represent hydrogen, halogen, trifluoromethyl, carboxyl, hydroxyl, straight-chain or branched alkoxy or alkoxycarbonyl with, in each case, up to 6 carbon atoms or straight-chain or branched alkyl with up to 6 carbon atoms, which in turn can be substituted by hydroxyl or by straight-chain or branched alkoxy with up to 4 carbon atoms,
- $R^1$ and $R^2$ are identical or different and represent hydrogen, cycloalkyl with 3 to 8 carbon atoms or straight-chain or branched alkyl with up to 10 carbon atoms, which is optionally substituted by cycloalkyl with 3 to 6 carbon atoms, or represent phenyl which is optionally substituted by halogen or trifluoromethyl, or
- $R^1$ and $R^2$ form, together with the carbon atom, a 4–8-membered cycloalkyl ring, and
- $R^3$ represents phenyl which is optionally substituted up to 3 times, identically or differently, by nitro, carboxyl, halogen, cyano or by straight-chain or branched alkenyl or alkoxycarbonyl with, in each case, up to 6 carbon atoms or by straight-chain or branched alkyl with up to 6 carbon atoms, which is optionally substituted by hydroxyl, carboxyl or by straight-chain or branched alkoxy or alkoxycarbonyl with, in each case, up to 6 carbon atoms, and/or is optionally substituted by a group of the formula —$OR^4$ or —$NR^5R^6$, in which
- $R^4$ is hydrogen or straight-chain or branched alkyl or alkenyl with, in each case, up to 6 carbon atoms,
- $R^5$ and $R^6$ are identical or different and denote phenyl, hydrogen or straight-chain or branched alkyl with up to 6 carbon atoms, or denote straight-chain or branched acyl with up to 8 carbon atoms, which is optionally substituted by a group of the formula —$NR^7R^8$, in which
- $R^7$ and $R^8$ are identical or different and denote hydrogen or straight-chain or branched acyl with up to 8 carbon atoms;

where appropriate in an isomeric form and the salts thereof.

The pyrimido[1,2-a]indoles according to the invention can also be in the form of their salts. Salts which may be generally mentioned here are those with organic or inorganic bases or acids.

Physiologically acceptable salts are preferred for the purpose of the present invention. Physiologically acceptable salts of the compounds according to the invention may be salts of the substances according to the invention with mineral acids, carboxylic acids or sulphonic acids. Particularly preferred examples are salts with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts may likewise be metal or ammonium salts of the compounds according to the invention which have a free carboxyl group. Particularly preferred examples are sodium, potassium, magnesium or calcium salts, and ammonium salts which are derived from ammonia or organic amines such as, for example, ethylamine, di- or triethylamine, di- or triethanolamine, dicyclohexylamine, dimethylaminoethanol, arginine, lysine, ethylenediamine or 2-phenylethylamine.

The compounds according to the invention can exist in stereoisomeric forms which either are related as image and mirror image (enantiomers) or are not related as image and mirror image (diastereomers). The invention relates to the enantiomers or diastereomers or mixtures thereof in each case. These mixtures of enantiomers and diastereomers can be separated into the stereoisomerically pure components in a manner known per se.

Preferred compounds of the general formula (I) are those in which
- A, D, E, G, L and M are identical or different and represent hydrogen, fluorine, chlorine, bromine, trifluoromethyl, carboxyl, hydroxyl, straight-chain or branched alkoxy or alkoxycarbonyl with, in each case, up to 4 carbon atoms or straight-chain or branched alkyl with up to 4 carbon atoms, which can in turn be substituted by hydroxyl or by straight-chain or branched alkoxy with up to 3 carbon atoms,
- $R^1$ and $R^2$ are identical or different and represent hydrogen, cyclopropyl, cyclobutyl, cyclopentyl, cyclohexyl, cycloheptyl, cyclooctyl or straight-chain or branched alkyl with up to 8 carbon atoms, which is optionally substituted by cyclopropyl, cyclopentyl or cyclohexyl, or represent phenyl which is optionally substituted by fluorine, chlorine or bromine, or
- $R^1$ and $R^2$ form, together with the carbon atom, a 4–7-membered cycloalkyl ring, and
- $R^3$ represents phenyl which is optionally substituted up to 3 times, identically or differently, by nitro, carboxyl, fluorine, chlorine, bromine, cyano, by straight-chain or branched alkenyl or alkoxycarbonyl with, in each case, up to 4 carbon atoms or by straight-chain or branched alkyl with up to 5 carbon atoms, which is optionally substituted by hydroxyl, carboxyl or by straight-chain or branched alkoxy or alkoxycarbonyl with, in each case, up to 5 carbon atoms, and/or is optionally substituted by a group of the formula —OR⁴ or —NR⁵R⁶,
in which
  R⁴ denotes hydrogen or straight-chain or branched alkyl or alkenyl with, in each case, up to 4 carbon atoms,
  R⁵ and R⁶ are identical or different and denote phenyl, hydrogen or straight-chain or branched alkyl with up to 5 carbon atoms, or straight-chain or branched acyl with up to 6 carbon atoms, which is optionally substituted by a group of the formula —NR⁷R⁸,
in which
  R⁷ and R⁸ are identical or different and denote hydrogen or straight-chain or branched acyl with up to 6 carbon atoms,
where appropriate in an isomeric form and the salts thereof.

Particularly preferred compounds of the general formula (I) are those in which
  A, D, E, G, L and M are identical or different and represent hydrogen, fluorine, chlorine, bromine, trifluoromethyl, carboxyl, hydroxyl, straight-chain or branched alkoxy or alkoxycarbonyl with, in each case, up to 3 carbon atoms or represents straight-chain or branched alkyl with up to 3 carbon atoms,
  R¹ and R² are identical or different and represent hydrogen, cyclopropyl, cyclobutyl, cyclopentyl, cyclohexyl, cycloheptyl, cyclooctyl or represent straight-chain or branched alkyl with up to 6 carbon atoms, which is optionally substituted by cyclopentyl or cyclohexyl, or represent phenyl which is optionally substituted by fluorine, chlorine or bromine, or
  R¹ and R² form, together with the carbon atom, a 5–7-membered cycloalkyl ring,
and
  R³ represents phenyl which is optionally substituted up to 3 times, identically or differently, by hydroxyl, trifluoromethyl, trifluoromethoxy, carboxyl, or by straight-chain or branched alkoxy, alkyl or alkoxycarbonyl with, in each case, up to 3 carbon atoms, where appropriate in an isomeric form and the salts thereof.

A process for the preparation of the compounds of the general formula (I) according to the invention has also been found and is characterized in that racemic or else already enantiomerically pure carboxylic acids or their activated derivatives of the general formula (II)

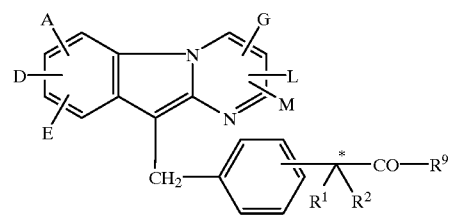

(II)

racemic or enantiomerically pure in which
  A, D, E, G, L, M, R¹ and R² have the indicated meaning, and
  R⁹ represents hydroxyl or represents an activating radical, preferably chlorine,
are amidated with phenylglycinols of the general formula (III)

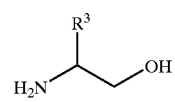

(III)

in which
  R³ has the indicated meaning,
  in inert solvents, where appropriate in the presence of bases and/or ancillary substances.

The process according to the invention can be illustrated by way of example by the following formula diagram:

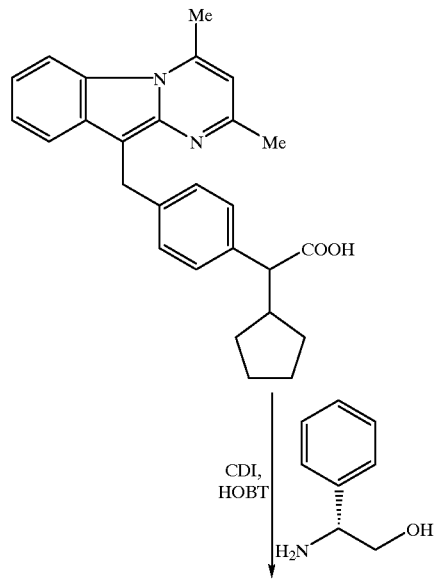

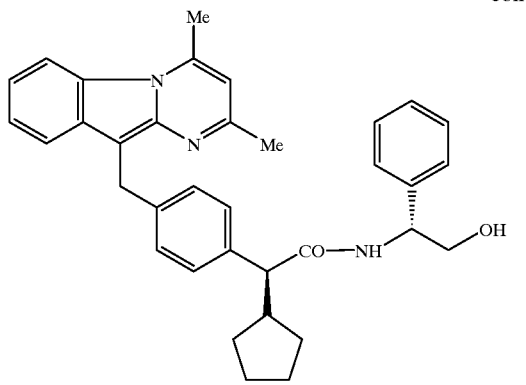 + 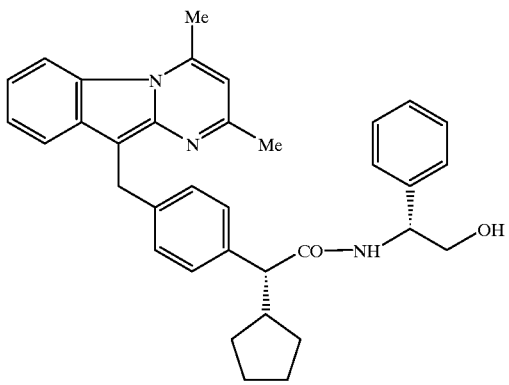

Suitable solvents for the amidation in this case are inert organic solvents which are not changed under the reaction conditions. These include ethers such as diethyl ether or tetrahydrofuiran, halogenated hydrocarbons such as dichloromethane, trichloromethane, tetrachloromethane, 1,2- dichloroethane, trichloroethane, tetrachloroethane, 1,2-dichloroethylene or trichloroethylene, hydrocarbons such as benzene, xylene, toluene, hexane, cyclohexane, or petroleum fractions, nitromethane, dimethylformamide, acetone, acetonitrile or hexamethylphosphoric triamide. It is likewise possible to employ mixtures of the solvents. Dichloromethane, tetrahydrofuran, acetone or dimethylformamide are particularly preferred.

Bases which can be employed for the process according to the invention are, in general, inorganic or organic bases. These preferably include alkali metal hydroxides such as, for example, sodium hydroxide or potassium hydroxide, alkaline earth metal hydroxides such as, for example, barium hydroxide, alkali metal carbonates such as sodium carbonate or potassium carbonate, alkaline earth metal carbonates such as calcium carbonate or alkali metal or alkaline earth metal alcoholates such as sodium or potassium methanolate, sodium or potassium ethanolate or potassium tert-butoxide, or organic amines (trialkyl ($C_1$–$C_6$)amines) such as triethylamine, or heterocycles such as 1,4-diazabicyclo[2.2.2]octane (DABCO), 1,8-diazabicyclo[5.4.0]undec-7-ene (DBU), pyridine, dimethylaminopyridine, methylpiperidine or morpholine. It is also possible to employ as bases alkali metals such as sodium and hydrides thereof such as sodium hydride. Sodium and potassium carbonates and triethylamine are preferred.

The base is employed in an amount of from 1 mol to 5 mol, preferably from 1 mol to 3 mol, based on 1 mol of the compound of the general formula (II).

The reaction is generally carried out at a temperature in the range from 0° C. to 150° C., preferably from +20° C. to +110° C.

The reaction can be carried out under atmospheric, elevated or reduced pressure (for example 0.5 to 5 bar). Atmospheric pressure is generally employed.

The reaction can, where appropriate, also take a course via the activated stage of the acid halides which can be prepared from the corresponding acids by reaction with thionyl chloride, phosphorus trichloride, phosphorus pentachloride, phosphorus tribromide or oxalyl chloride.

The bases listed above may also be employed as acid-binding aids for the amidation.

Likewise suitable as ancillary substances are dehydrating reagents. These include, for example, carbodiimides such as diisopropylcarbodiimide, dicyclohexylcarbodiimideorN-(3-dimethylaminopropyl)-N'-ethylcarbodiimide hydrochloride or carbonyl compounds such as carbonyldiimidazole or 1,2-oxazolium compounds such as 2-ethyl-5-phenyl-1,2-oxazolium-3'-sulphonate or propanephosphonic anhydride or isobutyl chloroformate or benzotriazolyloxy (dimethylamino)phosphonium hexafluorophosphate or diphenylphosphoryl azide or methanesulphonyl chloride, where appropriate in the presence of bases such as triethylamine or N-ethylmorpholine or N-methylpiperidine or dicyclohexylcarbodiimide and N-hydroxysuccinimide.

The ancillary substances are generally employed in an amount of from 0.5 to 3 mol, preferably from 1 to 1.5 mol, based on 1 mol of the appropriate carboxylic acids.

The carboxylic acids of the general formula (II) are novel and can be prepared by initially preparing, by reacting compounds of the general formula (IV)

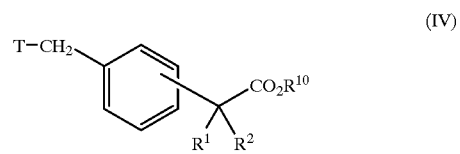

(IV)

in which $R^1$ and $R^2$ have the indicated meaning,

T represents a typical leaving group such as, for example, chlorine, bromine, iodine, tosylate or mesylate, and preferably represents bromine, and $R^{10}$ represents ($C_1$–$C_4$)-alkyl, with compounds of the general formula (V)

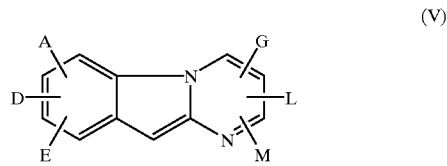

(V)

in which

A, D, E, G, L and M have the indicated meaning, the compounds of the general formula (VI)

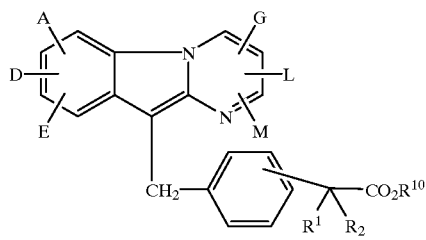
(VI)

in which
A, D, E, G, L, M, $R^1$, $R^2$ and $R^{10}$ have the abovementioned meaning,
in inert solvents, where appropriate in the presence of bases,
and subsequently hydrolysing the esters by conventional methods.

Enantiomerically pure acids of the formula (IIa) or (IIb):

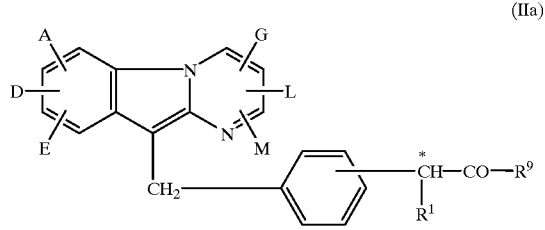
(IIa)

or

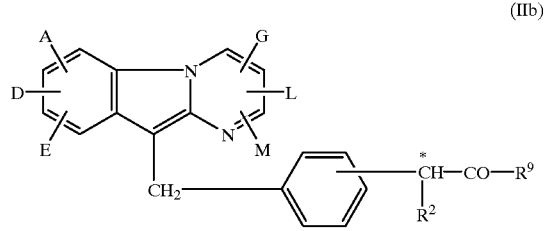
(IIb)

in which $R^1$ and $R^2$ are not hydrogen and $R^9$ represents hydroxyl, are furthermore obtained by preparing, from the D- or L-menthyl esters of the general formula (VII)

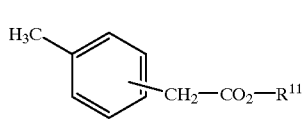
(VII)

in which
$R^{11}$ represents D- or L-menthyl,
by reaction with compounds of the general formula (VIIIa) or (VIIIb) $R^1$—Z (VIIIa) or $R^2$—Z (VIIIb)
in which
$R^1$ and $R^2$ have the indicated meaning, and
Z represents halogen, preferably bromine,
the enantiomerically pure menthyl esters of the general formula (IXa) or (IXb)

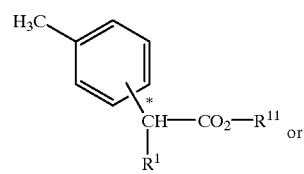
(IXa)

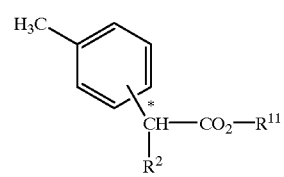
(IXb)

in which
$R^1$, $R^2$ and $R^{11}$ have the indicated meaning,
converting the latter in a next step by a halogenation into the compounds of the general formula (Xa) or (Xb)

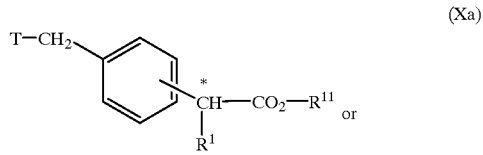
(Xa)

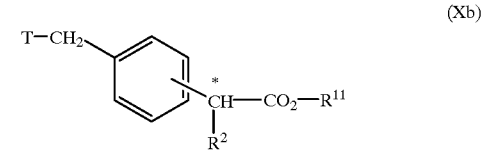
(Xb)

in which
$R^1$, $R^2$, and $R^{11}$ have the indicated meaning, and T represents halogen,
subsequently preparing, by reaction with the compounds of the general formula (V), the enantiomerically pure compounds of the general formula (XIa) or (XIb)

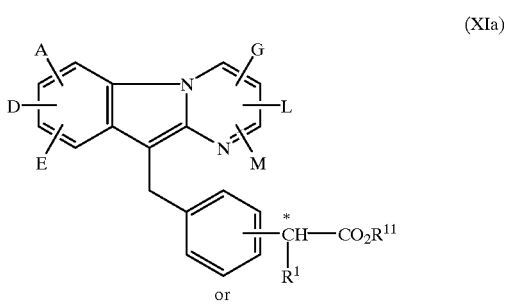
(XIa)

or

-continued

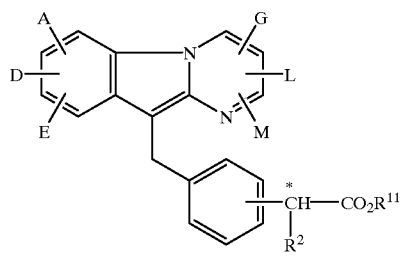
(XIb)

in which

A, D, E, G. L, M, $R^1$, $R^2$ and $R^{11}$ have the indicated meaning, or then converting the latter by hydrolysis into the enantiomerically pure acids of the general formula (IIa) and (IIb).

It is additionally possible to prepare enantiomerically pure acids of the formula (IIa) or (IIb) by initially converting racemic carboxylic acids of the general formula (XIIa) or (XIIb)

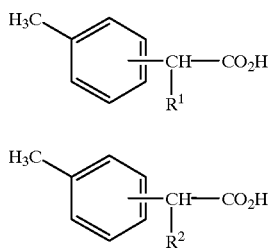
(XIIa)

(XIIb)

in which $R^1$ and $R^2$ have the indicated meaning, by reaction with (R)- or (S)-phenylethylamine in inert solvents and subsequent crystallization of the phenethylammonium salts and subsequent hydrolysis of the salts, into the enantiomerically pure compounds of the general formula (XIIIa) or (XIIIb)

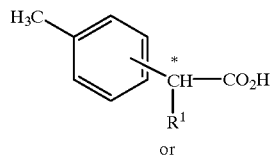
(XIIIa)

or (XIIIb)

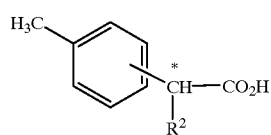

in which $R^1$ and $R^2$ have the indicated meaning, preparing from the latter in another step with isobutene, in inert solvents and in the presence of acids, the enantiomerically pure esters of the general formula (XIVa) or (XIVb)

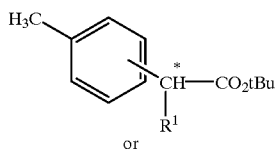
(XIVa)

or

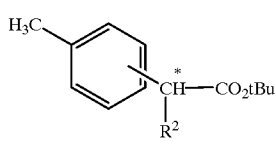
(XIVb)

converting the latter as described above by a halogenation into the enantiomerically pure compounds of the general formula (XVa) or (XVb)

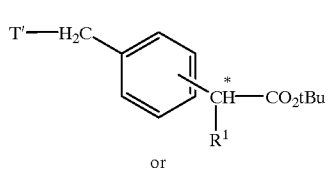
(XVa)

or

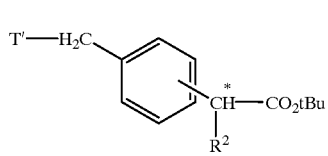
(XVb)

wherein $R^1$ and $R^2$ have the indicated meaning and T' represents halogen and converting the latter by reaction with the compounds of the general formula (V) into the enantiomerically pure esters of the general formula (XVIa) or (XVIb):

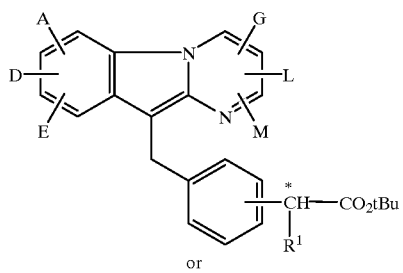
(XVIa)

or

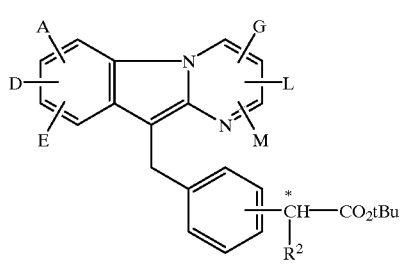
(XVIb)

in which A, D, E, G, L, M, $R^1$ and $R^2$ have the indicated meaning and in the final steps as described above, preparing the corresponding enantiomerically pure acids of the formula (IIa) or (IIb) and activated derivatives.

Solvents suitable for the processes are conventional organic solvents which are not changed under the reaction conditions. These preferably include ethers such as diethyl ether, dioxane, tetrahydrofuran, glycol dimethyl ether, or hydrocarbons such as benzene, toluene, xylene, hexane, cyclohexane or petroleum fractions, or halogenated hydrocarbons such as dichloromethane, trichloromethane, tetrachloromethane, dichloroethylene, trichloroethylene or chlorobenzene, or ethyl acetate, triethylamine, pyridine, dimethyl sulphoxide, dimethylformamide, hexamethylphosphoric triamide, acetonitrile, acetone or nitromethane. It is likewise possible to use mixtures of the said solvents. Dimethylformamide, toluene and tetrahydrofuran are preferred.

Bases which can be employed for the processes according to the invention are in general inorganic or organic bases. These preferably include alkali metal hydroxides such as, for example, sodium hydroxide or potassium hydroxide, alkaline earth metal hydroxides such as, for example, barium hydroxide, alkali metal carbonates and bicarbonates such as sodium carbonate, sodium bicarbonate or potassium carbonate, alkaline earth metal carbonates such as calcium carbonate, or alkali metal or alkaline earth metal alcoholates such as sodium or potassium methanolate, sodium or potassium ethanolate or potassium tert-butoxide, or organic amines (trialkyl($C_1$–$C_6$)-amines) such as triethylamine, or heterocycles such as 1,4-diazabicyclo[2.2.2]octane (DABCO), 1,8-diazabicyclo[5.4.0]undec-7-ene (DBU), pyridine, dimethylaminopyridine, methylpiperidine or morpholine. It is also possible to employ as bases alkali metals such as sodium or hydrides thereof such as sodium. hydride. Sodium bicarbonate, potassium carbonate and potassium tert-butoxide, DBU or DABCO are preferred.

Solvents suitable for the hydrolysis are water or the organic solvents customary for a hydrolysis. These preferably include alcohols such as methanol, ethanol, propanol, isopropanol or butanol, or ethers such as tetrahydrofuran or dioxane, or dimethylformamide, or dimethyl sulphoxide. Alcohols such as methanol, ethanol, propanol or isopropanol are particularly preferably used. It is likewise possible to employ mixtures of the said solvents.

The hydrolysis can, where appropriate, also be carried out with acids such as, for example, trifluoroacetic acid, acetic acid, hydrochloric acid, hydrobromic acid, methanesulphonic acid, sulphuric acid or perchloric acid, preferably with trifluoroacetic acid.

The hydrolysis is generally carried out at a temperature in the range from 0° C. to +100° C., preferably from +20° C. to +80° C.

The hydrolysis is generally carried out under atmospheric pressure. However, it is also possible to employ reduced pressure or elevated pressure (for example from 0.5 to 5 bar).

When carrying out the hydrolysis, the base is generally employed in an amount of from 1 to 3 mol, preferably from 1 to 1.5 mol, based on 1 mol of the ester. Equimolar amounts of the reactants are particularly preferably used.

The hydrolysis of tert-butyl esters is generally carried out with acids such as, for example, hydrochloric acid or trifluoroacetic acid, in the presence of one of the abovementioned solvents and/or water or mixtures thereof preferably with dioxane or tetrahydrofuran.

General process [A] according to the invention is generally carried out at a temperature in the range from −30° C. to +150° C., preferably from 80° C. to 150° C.

Suitable and preferred conditions for the individual steps to prepare enantiomerically pure acids are the following:

Compounds of the general formula (IXa) and (IXb) are preferably prepared in dimethylformamide and potassium tert-butanolate at a temperature in the range from −10° C. to +10° C.

Halogenation to give the compounds of the general formula (Xa) and (Xb) is carried out in chlorobenzene with 1,3-dibromo-5,5-dimethylhydantoin in the presence of azobisisobutyronitrile at a temperature in the range from 0° C. to 110° C.

The reaction to give the compounds of the general formula (XIa) and (XIb) takes place under a protective gas atmosphere in dimethylformamide and potassium tert-butanolate at a temperature in the range from 0° C. to 30° C.

Hydrolysis of the compounds of the general formula (XIa) and (XIb) can be carried out as described above, with the HBr/formic acid system being particularly preferred. The hydrolysis is carried out at a temperature in the range from 20° C. to 100° C.

Suitable and preferred activating reagents are trifluoromethanesulphonyl chloride, mesyl chloride, oxalyl chloride and thionyl chloride. Thionyl chloride is particularly preferred.

The reaction to give the compounds of the general formula (XIIIa) and (XIIIb) takes place in the first step preferably in tetrahydrofuran and triethylamine, and in the second step in the water/hydrochloric acid system. The reaction is carried out at a temperature in the range from 30° C. to 70° C.

Concentrated sulphuric acid is particularly preferably employed as acid for preparing the compounds of the general formula (XIVa) and (XIVb) according to the invention. The preparation is carried out with methylene chloride.

In the further work-up step, potassium carbonate is employed as base. The reaction takes place at a temperature in the range from 0° C. to +20° C., particularly preferably at 10° C.

The compounds of the general formula (XIVa) and (XIVb) are halogenated with N-bromosuccinimide in methylene chloride in the presence of azobisisobutyronitrile.

The base is generally employed in an amount of from 0.05 mol to 10 mol, preferably from 1 mol to 2 mol, in each case based on 1 mol of the compounds of the general formulae (IV), (VIIIa) and (VIIIb) and (XIa) and (XIb).

The processes according to the invention are generally carried out under atmospheric pressure. However, it is also possible to carry out the process under elevated pressure or under reduced pressure (for example in a range from 0.5 to 5 bar).

The compounds of the general formula (III) are known per se.

The compounds of the general formula (IV), (VIIIa) and (VIIIb) are known or can be prepared in analogy to known methods.

The compounds of the general formula (V) are in some cases known or novel, but can then be prepared in analogy to published methods.

The compounds of the general formula (VII) are novel as species and are prepared from the corresponding acid.

The enantiomerically pure compounds of the general formula (IXa) and (IXb) are, with the exception of $R^1$ or $R^2$=isopropyl, novel and can be prepared as described above.

The compounds of the general formulae (Xa), and (Xb), (XIa), (XIb) are novel and can be prepared as described above.

The compounds of the general formula (XIVa) and (XIVb) are in some cases known or can be prepared by customary methods.

The enantiomerically pure compounds of the general formula (XVa) and (XVb) and (XVIa) and (XVIb) are novel and can be prepared as described above.

The compounds of the general formula (VI) are novel and can be prepared as described above.

The compounds of the general formula (I) according to the invention have a spectrum of pharmacological effects which was unpredictable.

They can be used as active compounds in medicaments for reducing changes in vessel walls and for treating coronary heart disease, heart failure, brain dysfunction, ischaemic brain disease, stroke, disturbances of blood flow, microcirculation disturbances and thromboses.

Furthermore, proliferation of smooth muscle cells plays a crucial part in the occlusion of vessels. The compounds according to the invention are suitable for inhibiting this proliferation and thus preventing atherosclerotic processes.

The compounds according to the invention are distinguished by lowering the ApoB 100-associated lipoproteins (VLDL and its breakdown products such as, for example, LDL), and ApoB 100, the triglycerides and cholesterol. Hence they have valuable pharmacological properties which are superior by comparison with the prior art.

Surprisingly, the effect of the compounds according to the invention initially comprises reducing or completely inhibiting the formation and/or the release of ApoB 100-associated lipoproteins from liver cells, which results in a lowering of the VLDL plasma level. This VLDL lowering must be associated with a lowering of the plasma levels of ApoB 100, LDL, triglycerides and cholesterol; thus a plurality of the abovementioned risk factors involved in changes in vessel walls are reduced simultaneously.

The compounds according to the invention can therefore be employed for the prevention and treatment of atherosclerosis, of obesity, pancreatitis and of constipation.

1. Inhibition of the Release of ApoB 100-associated Lipoproteins

The test to detect inhibition of the release of ApoB 100-associated lipoproteins from liver cells took place in vitro with cultivated liver cells, preferably with cells of the human line HepG2. These cells are cultured under standard conditions in medium for culturing eukaryotic cells, preferably in RPMI 1640 with 10% fetal calf serum. HepG2 cells synthesize, and secrete into the culture supernatant, ApoB 100-associated lipoprotein particles which in principle have a similar structure to the VLDL and LDL particles to be found in the plasma.

These particles can be detected using an immunoassay for human LDL. This immunoassay takes place with antibodies which had been induced against human LDL in rabbits under standard conditions. The anti-LDL antibodies (rab anti-LDL Abs) were purified by affinity chromatography on an immunosorbent with human LDL. These purified rab anti-LDL Abs are adsorbed onto the surface of plastic. This adsorption expediently takes place onto the plastic surface of microtitre plates with 96 wells, preferably on MaxiSorp plates. If ApoB 100-associated particles are present in the supernatant from Hep G2 cells, thesearticles can bind to the insolubilized rab anti-LDL Abs, resulting in an immune complex which is bound to the plastic surface. Unbound proteins are removed by washing. The immune complex present on the plastic surface is detected using monoclonal antibodies which had been induced against human LDL, and had been purified, under standard conditions. These antibodies were conjugated to the enzyme peroxidase. Peroxidase converts the colourless substrate TMB into a coloured product in the presence of $H_2O_2$. After acidification of the reaction mixture with $H_2SO_4$, the specific absorption of light at 450 nm is determined and is a measure of the amount of ApoB 100-associated particles secreted into the culture supernatant by the HepG2 cells.

Surprisingly, the compounds according to the invention inhibit the release of ApoB 100-associated particles. The $IC_{50}$ indicates the concentration of substance at which the absorption of light is inhibited by 50% compared with the control (solvent control without substance).

| Ex. No. | Apo B $IC_{50}$ [nM] |
| --- | --- |
| 2 | 1.3 |
| 18 | 1.9 |
| 24 | 0.6 |
| 36 | 1.1 |
| 54 | 0.7 |
| 57 | 2.7 |

2. Determination of VLDL Secretion in Vivo in Hamsters

The effect of the test substances on VLDL secretion in vivo is investigated on hamsters. To do this, golden hamsters are premedicated with atropine (83 mg/kg s.c.) and then anaesthetized with Ketavet (83 mg/kg s.c.) and Nembutal (50 mg/kg i.p.). When the animals' reflexes have been lost, the jugular vein is exposed and cannulated. Subsequently, 0.25 ml/kg of a 20% strength solution of Triton WR-1339 in physiological saline is administered. This detergent inhibits lipoprotein lipase and thus leads to an increase in the triglyceride level because there is no catabolism of secreted VLDL particles. This triglyceride increase can be used as a measure of the VLDL secretion rate. Blood is taken from the animals by puncture of the retroorbital venous plexus before and one and two hours after administration of the detergent. The blood is incubated at room temperature for two hours and then at 4° C. overnight in order to complete the coagulation. It is then centrifuged at 10,000 g for 5 minutes. The triglyceride concentration in the serum obtained in this way is determined using a modified commercially obtainable enzyme assay (Merckotest® Triglyceride No. 14354). 100 μl of serum are mixed with 100 μl of assay reagent in 96-well plates and incubated at room temperature for 10 minutes. Subsequently, the optical density is determined at a wavelength of 492 nm in an automatic plate reader (SLT Spectra). Serum samples with a triglyceride concentration which is too high are diluted with physiological saline. The triglyceride concentration present in the samples is determined using a standard plot measured in parallel. In this model, test substances are administered either intravenously immediately before administration of the detergent or orally or subcutaneously before induction of anaesthesia.

3. Inhibition of Intestinal Triglyceride Absorption in Vivo (Rats)

Substances to be investigated for their inhibitory effect on triglyceride absorption in vivo are administered orally to male Wistar rats with a body weight between 170 and 230 g. For this purpose, the animals are divided into groups of 6 animals 18 hours before administration of the substance and then their food is withdrawn. Drinking water is available to the animals ad libitum. The animals in the control groups receive an aqueous tragacanth suspension or a tragacanth suspension which contains olive oil. The tragacanth/olive oil suspension is prepared using an Ultra-Turrax. The substances to be investigated are suspended in a corresponding tragacanth/olive oil suspension, likewise with an Ultra-Turrax, immediately before administration of the substances.

Blood is taken from each rat by puncture of the retroorbital venous plexus to determine the baseline serum triglyceride content before the administration by gavage. Subsequently, the tragacanth suspension, the tragacanth/olive oil suspension without substance (control animals) or the substances suspended in a corresponding tragacanth/olive oil suspension are administered to the fasting animals by gavage. Further blood is taken to determine the postprandial serum triglyceride increase as a rule 1, 2 and 3 hours after the administration by gavage.

The blood samples are centrifuged and, after obtaining the serum, the triglycerides are determined by photometry using an EPOS analyser 5060 (Eppendorf Gerätebau, Neteheler & Hinz GmbH, Hamburg). The triglycerides are determined fully enzymatically using a commercially available UV assay.

The postprandial serum triglyceride increase is calculated by subtracting the initial triglyceride level for each animal from its corresponding postprandial triglyceride concentrations (1, 2 and 3 hours after administration).

The differences (in mmol/l) at each time (1, 2 and 3 hours) are averaged for the groups, and the averages for the serum triglyceride increase ($\Delta TG$) for the animals treated with the substance are compared with the animals which received only the tragacanth/oil suspension.

The changes in serum triglycerides for the control animals which received only tragacanth are calculated in the same way. The effect of the substance at each time (1, 2 or 3 hours) is calculated as follows and reported in $\Delta \%$ of the control receiving the oil.

$$\Delta\% \text{ triglyceride increase} = \frac{\Delta TG_{substance} - \Delta TG_{tragacanth\ control}}{\Delta TG_{oil\ intake} - \Delta TG_{tragacanth\ control}} \times 100$$

The statistical analysis is carried out with Student's t test after previous checking of the variances for homogeneity.

Substances which reduce the postprandial serum triglyceride increase, compared with the untreated control group, statistically significantly ($p<0.05$) by at least 30% at one time are regarded as pharmacologically active.

4. Inhibition of VLDL Secretion in Vivo (Rats)

The effect of test substances on VLDL secretion is likewise investigated on rats. For this purpose, 500 mg/kg of body weight (2.5 mg/kg) of Triton WR-1339 dissolved in physiological saline are administered intravenously into the tail vein of rats. Triton WR-1339 inhibits lipoprotein lipase and thus, through inhibition of VLDL catabolism, leads to an increase in the triglyceride and cholesterol levels. These increases can be used as a measure of the VLDL secretion rate.

Blood is taken from the animals by puncture of the retroorbital venous plexus before and two hours after administration of the detergent. The blood is incubated at room temperature for 1 h for coagulation, and the serum is obtained by centrifugation at 10 000 g for 20 s. The triglycerides are subsequently determined using a commercial coupled enzyme assay (Sigma Diagnostics®, No. 339) by photometry at a wavelength of 540 nm. Measurement takes place with the aid of a likewise coupled enzyme assay (Boehringer Mannheim®, No. 1442350) at a wavelength of 546 nm. Samples with triglyceride and cholesterol concentrations which exceed the range of measurement of the methods are diluted with physiological saline. The serum concentrations in each case are found by means of standard series measured in parallel. Test substances are administered orally, intravenously or subcutaneously immediately after the Triton injection.

The invention additionally relates to the combination of novel pyrimido[1,2-b]indoles of the general formula (I) with a glucosidase and/or amylase inhibitor for the treatment of familial hyperlipaemia, of obesity (adiposity) and of diabetes mellitus. Glucosidase and/or amylase inhibitors for the purpose of the invention are, for example, acarbose, adiposine, voglibose, miglitol, emiglitate, MDL-25637, camiglibose (MDL-73945), tendamistat, AL-3688, trestatin, pradimicin-Q and salbostatin.

A combination of acarbose, miglitol, emiglitate or voglibose with one of the compounds according to the invention, of the general formula (I) detailed above, is preferred.

The novel active compounds can be converted in a known manner into conventional formulations such as tablets, coated tablets, pills, granules, aerosols, syrups, emulsions, suspensions and solutions, using inert, non-toxic, pharmaceutically suitable excipients or solvents. The therapeutically active compound should be present in these in a concentration of, in each case, about 0.5 to 90% by weight of the complete mixture, that is to say in amounts which are sufficient to achieve the stated dose range.

The formulations are produced, for example, by extending the active compounds with solvents and/or excipients, where appropriate with use of emulsifiers and/or dispersants, it being possible, for example in the case where water is used as diluent, to use organic solvents as auxiliary solvents where appropriate.

Administration takes place in a conventional way, preferably orally or parenterally, in particular perlingually or intravenously.

In the case of parenteral administration, it is possible to employ solutions of the active compound using suitable liquid vehicles.

In general it has proved advantageous to administer, in order to achieve effective results, amounts of about 0.001 to 1 mg/kg, preferably about 0.01 to 0.5 mg/kg, of body weight on intravenous administration, and the dosage on oral administration is about 0.01 to 20 mg/kg, preferably 0.1 to 10 mg/kg, of body weight.

It may nevertheless be necessary where appropriate to depart from the stated amounts, in particular depending on the body weight and the mode of administration, the individual response to the medicament, the nature of its formulation and the time or interval over which administration takes place. Thus, it may suffice in some cases to manage with less than the abovementioned minimum amount, whereas in other cases the upper limit mentioned must be exceeded. In the case of administration of relatively large amounts, it may be advisable to divide these into several individual doses over the day.

Abbreviations:
Ac=acetyl
AIBN=azobisisobutyronitrile
Bn=benzyl
Bz=benzoyl
cDec=cyclodecyl
CDI=N'-(3-dimethylaminopropyl)-N-ethylcarbodiimide hydrochloride
cDodec=cyclododecyl
cHept=cycloheptyl
cHex=cyclohexyl
cNon=cyclononyl
cOct=cyclooctyl
cPent=cyclopentyl
cPr=cyclopropyl
18-crown-6=1,4,7,10,13,16-hexaoxacyclooctadecane
cUndec=cycloundecyl DCC=dicyclohexylcarbodiimide
DDQ=2,3-dichloro-5,6-dicyano-1,4-benzoquinone
dia=diastereomer
dia A=diastereomer with the larger $R_f$
dia B=diastereomer with the smaller $R_f$
DMAP=4-(N,N-dimethylamino)pyridine
DME=1,2-dimethoxyethane
DMF=N,N-dimethylformamide
DMSO=dimethyl sulphoxide
ent=enantiomer
Et=ethyl
HOBT=1-hydroxy-1H-benzotriazole
iBu=isobutyl
ipent=isopentyl
iPr=isopropyl
Me=methyl
Ment=(L)-menthyl
Mes=mesyl
NBS=N-bromosuccinimide
nBu=normal butyl
nHex=normal hexyl
nPent=normal pentyl
nPr=normal propyl
Ph=phenyl
PPA=polyphosphoric acid
pTol=para-tolyl
pTos=para-tosyl
rac=racemate
sBu=secondary butyl
tBu=tertiary butyl
TFA=trifluoroacetic acid
THF=tetrahydrofuran
TMS=tetramethylsilane Method for Preparing the Mobile Phase BABA 87.9 ml of an aqueous 0.06667 molar potassium dihydrogen phosphate solution and 12.1 ml of an aqueous 0.06667 molar disodium hydrogen phosphate solution are mixed. 60 ml of the solution prepared in this way are shaken with 200 ml of n-butyl acetate, 36 ml of n-butanol and 100 ml of glacial acetic acid, and the aqueous phase is separated off. The organic phase is the mobile phase BABA.

| Solvent mixtures used | |
| --- | --- |
| Solvent | Designation |
| Petroleum ether: ethyl acetate = 20:1 | A |
| Petroleum ether: ethyl acetate = 2:1 | B |
| Petroleum ether: ethyl acetate = 5:1 | C |
| Dichloromethane: ethanol = 20:1 | D |
| Petroleum ether: ethyl acetate = 1:1 | E |
| Dichloromethane: ethanol = 50:1 | F |
| Dichloromethane | G |
| Petroleum ether: ethyl acetate = 9:1 | H |
| Dichloromethane: methanol = 19:1 | I |
| Petroleum ether: ethyl acetate = 4:1 | J |
| Dichloromethane: methanol = 100:1 | K |
| Dichloromethane: methanol = 100:3 | L |
| Toluene | M |
| Toluene: ethyl acetate = 9:1 | N |
| Toluene: ethyl acetate = 2:1 | O |
| Petroleum ether: ethyl acetate = 10:1 | P |
| Petroleum ether: ethyl acetate = 20:1 | Q |
| Petroleum ether | R |
| Petroleum ether: ethyl acetate = 6:1 | XA |

Starting Compounds

EXAMPLE I

Methyl 4-tolylacetate

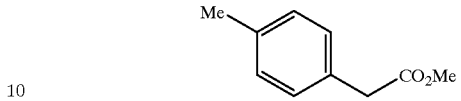

300 g(1.998 mol) of 4-tolylacetic acid are dissolved in 2.5 l of methanol, stirred with 100 ml of concentrated sulphuric acid and boiled under reflux for 2.5 h. Then a total of 430 g (5.1 mol) of sodium bicarbonate are gradually stirred in (evolution of carbon dioxide), the methanol is substantially evaporated off in vacuo, the residue is partitioned between water and dichloromethane, and the aqueous phase is back-extracted with dichloromethane. The combined organic phases are dried with sodium sulphate, and solvent is removed in vacuo. The residue is distilled under high vacuum.

Yield: 336 g.

Boiling point: 65° C. (0.5 mbar)

$R_f$=0.81 (toluene:ethyl acetate=2:1)

EXAMPLE II

Ethyl 4-tolylacetate

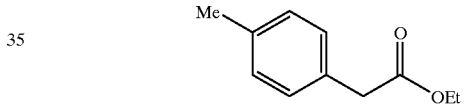

Ethyl 4-tolylacetate is prepared in analogy to the method in Example 1 starting from 4-tolylacetic acid.

$R_f$=0.43 (A)

EXAMPLE III tert-Butyl 4-methylphenylacetate

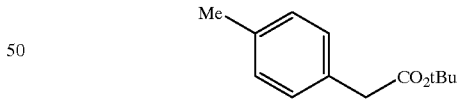

450 g (3 mol) of 4-methylphenylacetic acid, 1.13 l (12 mol) of tert-butanol and 90 g (0.74 mol) of dimethylamiopyridine are dissolved in 2 l of dichloromethane. Addition of 680 g (3.3 mol) of dicyclohexylcarbodiimide dissolved in 400 ml of dichloromethane is followed by stirring at 25° C. for 20 h, the precipitated urea is filtered off with suction and washed with 200 ml of dichloromethane, and the organic phase is washed twice each with 500 ml of 2 M hydrochloric acid and water. The organic phase is dried with sodium sulphate, concentrated and distilled.

Yield: 408 g (66%)

Boiling point: 73–78° C. (0.2 torr).

EXAMPLE IV tert-Butyl (2R/2S)-2-cyclopentyl-2-(4-methylphenyl)acetate

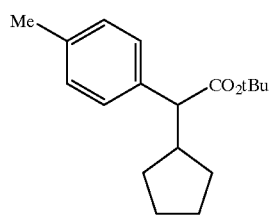

33.5 g (0.3 mol) of potassium tert-butoxide are introduced into 100 ml of DMF with exclusion of moisture at 0° C., and 51.6 g (0.25 mol) of the compound from Example III in 250 ml of DMF are added dropwise. The mixture is stirred at 0° C. for 30 min, 32.2 ml (0.3 mol) of cyclopentyl bromide in 150 ml of DMF are added dropwise at 5–15° C., and the mixture is stirred at 25° C. for 20 h. After concentration, the residue is partitioned between water and diethyl ether, and the ether phase is dried over sodium sulphate and concentrated. The product crystallizes out.

Yield: 67 g (97.5%)

Solidification point: 51–53° C.

The racemic compounds in Table I are prepared in analogy to the method in Example IV:

TABLE I

| Ex. No | —X | —Y | a) m.p.(° C.) b) $R_f$ (solvent) | Spectra | Starting material from Ex. No. |
|---|---|---|---|---|---|
| V | —$CH_3$ = Me | —$C(CH_3)_3$ = tBu | b) 0.71 (M) | | III |
| VI | —$C_2H_5$ = Et | tBu | b) 0.67 (M) | | III |
| VII | —$CH_2CH_2CH_3$ = nPr | tBu | b) 0.69 (M) | | III |
| VIII | —$CH(CH_3)_2$ = iPr | Me | b) 0.86 (O) | | I |
| IX | —$CH(CH_3)_2$ = iPr | tBu | b) 0.76 (N) | | III |
| X | —$CH_2CH_2CH_2CH_3$ = nBu | tBu | b) 0.74 (M) | | III |
| XI | —$CH_2CH(CH_3)_2$ = iBu | tBu | b) 0.70 (M) | | III |
| XII | —$CH_2CH_2CH_2CH_2CH_3$ = nPent | tBu | b) 0.75 (H) | | III |
| XIII | —$CH_2CH_2$—$CH(CH_3)_2$ = iPent | tBu | b) 0.51 (P) | | III |
| XIV | —$CH(CH_2CH_3)_2$ | tBu | | MS: 276 ($M^+$, 4%) | III |
| XV | —$CH_2CH_2CH_2CH_2CH_2CH_3$ = nHex | tBu | b) 0.75 (M) | | III |
| XVI | —$CH_2CH(CH_2CH_3)_2$ | tBu | | MS: 290 ($M^+$, 1%) | III |
| XVII | = cPent | Me | b) 0.59 (P) | | I |
| XVIII | = cHex | Me | b) 0.62 (Q) | | I |

TABLE I-continued

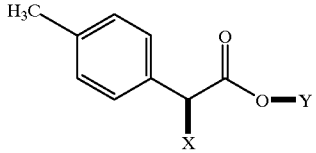

| Ex. No | —X | —Y | a) m.p.(° C.) b) R$_f$ (solvent) | Spectra | Starting material from Ex. No. |
|---|---|---|---|---|---|
| XIX | cHex | tBu | b) 0.72 (M) | | III |
| XX | = cHept  | Me | b) 0.57 (M) | | I |
| XXI | cHept | tBu | b) 0.67 (M) | | III |
| XXII | = cOct 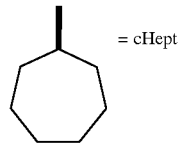 | tBu | b) 0.77 (M) | | III |
| XXIII | 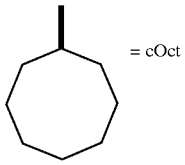 | tBu | b) 0.86 (Q) | | III |
| XXIV | 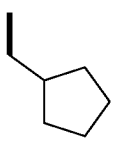 | tBu | b) 0.82 (N) | | III |

The compounds in Table II are prepared in analogy to the method in Example IV; only 2.5 equivalents of the base and 2.5 equivalents of the halogenoalkane (in the case of the cyclic alkyl radicals 1.2 equivalents of the α,ω-dihalogenoalkane) are employed.

TABLE II

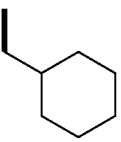

| Ex. No. | —X | —Y | a) m.p. (° C.) b) R$_f$ (solvent) | Spectra | Starting material from Ex. No. |
|---|---|---|---|---|---|
| XXV | 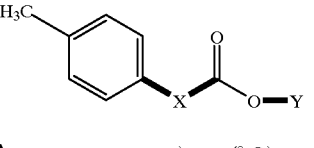 | tBu | b) 0.68 (F) | | III |
| XXVI |  | tBu | b) 0.32 (R) | | III |

TABLE II-continued

| Ex. No. | —X | —Y | a) m.p. (° C.)<br>b) $R_f$ (solvent) | Spectra | Starting material from Ex. No. |
|---|---|---|---|---|---|
| XXVII | H₃C(H₂C)₂—C—(CH₂)₂CH₃ | tBu | b) 0.84 (B) | | III |
| XXVIII | H₃C(H₂C)₃—C—(CH₂)₃CH₃ | tBu | b) 0.82 (C) | | III |
| XXIX | cyclopentyl | tBu | b) 0.23 (R) | | III |
| XXX | cyclohexyl | tBu | b) 0.21 (R) | | III |
| XXXI | cycloheptyl | tBu | b) 0.26 (R) | | III |

EXAMPLE XXXII tert-Butyl (2R/2S)-2-(4-bromomethylphenyl)-2-cyclopentylacetate

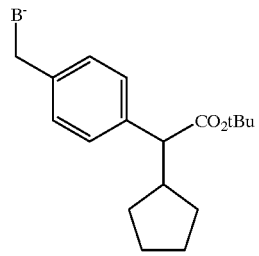

27.4 g (0.1 mol) of the compound from Example IV are dissolved in 200 ml of tetrachloromethane and heated to boiling. Addition of 0.82 g of azobisisobutyronitrile is followed by addition of 18.7 g (0.105 mol) of N-bromosuccinimide in portions, and the mixture is subsequently refluxed for 1 h, cooled to 0° C. and filtered to remove succinimide. The product precipitates after concentration of the filtrate. It is washed with petroleum ether (40/60) and dried.

Yield: 20 g (57%)

Solidification point: 73–76° C.

The racemic compounds in Table III are prepared in analogy to the method for Example No. XXXII:

TABLE III

[Structure: 4-(bromomethyl)phenyl group attached to CH(X)-C(=O)-O-Y]

| Ex. No. | ━X | ━Y | a) m.p. (° C.)<br>b) R_f (Solvent) | Spectra | Starting material from Ex. No. |
|---|---|---|---|---|---|
| XXXIII | ━H | Me | b) 0.45 (XA) | | I |
| XXXIV | ━H | tBu | b) 0.54 (H) | MS: 302, 304<br>[M + NH$_4$]$^+$; 100%, 98%) | III |
| XXXV | Me | tBu | b) 0.78 (M) | | V |
| XXXVI | Et | tBu | b) 0.75 (M) | | VI |
| XXXVII | nPr | tBu | b) 0.80 (M) | | VII |
| XXXVIII | iPr | Me | b) 0.78 (G) | | VIII |
| XXXIX | iPr | tBu | b) 0.90 (N) | | IX |
| XL | nBu | tBu | b) 0.82 (M) | | X |
| XLI | iBu | tBu | b) 0.86 (G) | | XI |
| XLII | nPent | tBu | b) 0.73 (H) | | XII |
| XLIII | iPent | tBu | | MS: 372, 374<br>[M + NH$_4$]$^+$; 79%, 77%) | XIII |
| XLIV | ━CH(CH$_2$CH$_3$)$_2$ | tBu | | MS: 372, 372<br>([M + NH$_4$]$^+$; 4%, 4%) | XIV |
| XLV | nHex | tBu | b) 0.85 (M) | | XV |
| XI, VI | ━CH$_2$CH(CH$_2$CH$_3$)$_2$ | tBu | | MS: 386, 388<br>([M + NH$_4$]$^+$; 14%, 14%) | XVI |
| XI, VII | cPent | Me | b) 0.63 (P) | | XVII |
| XI, VIII | cHex | Me | b) 0.47 (Q) | | XVIII |
| IL | cHex | tBu | b) 0.58 (P) | | XIX |
| L | cHept | Me | b) 0.59 (M) | | XX |
| LI | cHept | tBu | b) 0.34 (G) | | XXI |
| LII | cOct | tBu | b) 0.49 (Q) | | XXII |
| LIII | ━CH$_2$-cyclopentyl | tBu | b) 0.58 (A) | | XXIII |
| LIV | ━CH$_2$-cyclohexyl | tBu | | $^1$H-NMR (250 MHz, CDCl$_3$, TMS);<br>δ = 3.58 (m, 1H), 4.49 (S, 2H) ppm | XXIV |

The compounds in Table IV are prepared in analogy to the method in Example XXXII:

TABLE IV (Structure: 4-(bromomethyl)phenyl with X-C(=O)-O-Y group)

| Ex. No. | —X (group) | —Y | a) m.p. (° C.) b) R_f (solvent) Spectra | Starting material from Ex. No. |
|---|---|---|---|---|
| LV | C(CH_3)_2 (H_3C, CH_3) | tBu | b) 0.68 (F) | XXV |
| LVI | C(OCH_2CH_3)(CH_2CH_3) | tBu | b) 0.38 (Q) | XXVI |
| LVII | C((CH_2)_2CH_3)_2 | tBu | b) 0.84 (B) | XXVII |
| LVIII | C((CH_2)_3CH_3)_2 | tBu | b) 0.82 (C) | XXVIII |
| LIX | cyclopentyl | tBu | MS: 356, 358 ([M + NH_4]^+: 9%, 11%) | XXIX |
| LX | cyclohexyl | tBu | MS: 370, 372 ([M + NH_4]^+: 5%, 5%) | XXX |
| LXI | cycloheptyl | tBu | b) 0.47 (Q) | XXXI |

EXAMPLE LXII
Ethyl (2R/2S)-2-(2-nitrophenyl)-2-cyanoacetate

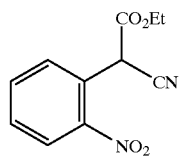

93.4 g (832 mmol) of potassium tert-butanolate and 92.4 ml (868 mmol) of ethyl cyanoacetate are stirred with 680 ml of tert-butanol at about 20° C. [compare C. A. Grob and O. Weissbach, Helv. Chim. Acta 44, 1748 (1961)]. After 30 minutes, a solution of 63 g (400 mmol) of 2-chloronitrobenzene in 150 ml of tert-butanol which has been preheated to about 60° C. is run in and the mixture is boiled under reflux for 10 hours. The reaction solution is cooled to about 20° C. and adjusted to a pH of 3 with 2 M hydrochloric acid and subsequently evaporated in a water bath at 40° C. (30 mbar). The residue is poured into 1 l of diethyl ether and 500 ml of water, and the organic phase is separated off and washed several times with aqueous sodium bicarbonate solution and then with water. The solution is dried with magnesium sulphate and evaporated, and the crude product is purified by chromatography on silica gel 60 (Merck/40–63 µm/petroleum ether:ethyl acetate=3:1).

Yield: 67.7 g (289 mmol) 72% of theory.
TLC: $R_f$=0.46 (B).
$^1$H-NMR (CDCl_3, 250 MHz, TMS): δ=1.33 (t, 3H); 4.31 (q, 2H); 5.68 (s, 1H); 7.65 (m, 1H); 7.73–7.81 (m, 2H); 8.23 (m, 1H) ppm.

The racemic compounds in Table V are prepared in analogy to the method in Example LXII.

TABLE V

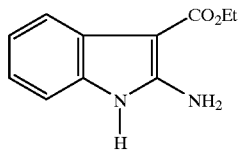

| Ex. No. | A | a) m.p. (° C.)<br>b) $R_f$ (solvent) | Spectra | Starting material from Ex. No. |
|---|---|---|---|---|
| LXIII | 4-Cl | | MS (Cl, NH$_3$): 286 ([M + NH$_4$]$^+$; 73%) | |
| LXIV | 5-OMe | b) 0.53 (G) | | |
| LXV | 4-OMe | b) 0.47 (G) | | |

EXAMPLE LXVI
2-Amino-3-ethoxycarbonylindole

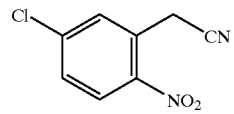

20 g (85.4 mmol) of the compound from Example LXII are heated to 100° C. in 300 ml of acetic acid, a total of 15 g (268 mmol) of iron powder are added in portions with vigorous stirring, and the mixture is boiled under reflux for 45 minutes [compare C. A. Grob and O. Weissbach, Helv. Chim. Acta 44, 1748 (1961)]. After cooling to about 20° C., the mixture is filtered with suction through a Seitz filter and washed with 100 ml of acetic acid. The filtrate is substantially evaporated and taken up again with diethyl ether and water, and the organic phase is extracted with aqueous potassium bicarbonate solution. The collected aqueous phases are adjusted to pH=3–4 with 2 M hydrochloric acid and extracted by shaking with diethyl ether. Finally, the combined organic phases are dried with magnesium sulphate and evaporated. The crude product is purified by chromatography on silica gel 60 (Merck/40–63 μm/petroleum ether: ethyl acetate=2:1 to 1:1).

Yield: 9.9 g (48.5 mmol) 57% of theory.
TLC: $R_f$=0.35 (E).
$^1$H-NMR (d$_6$-DMSO, 200 MHz, TMS): δ=1.32 (t, 3H); 4.21 (q, 2H); 6.68 (s, br, 2H); 6.82–6.92 (m, 2H); 7.10 (m, 1H); 7.54 (m, 1H); 10.64 (s, br, 1H) ppm.

EXAMPLE LXVII
2-Aminoindole hydrochloride

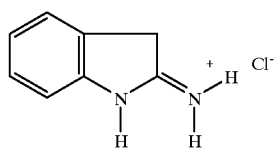

30 g (147 mmol) of the compound from Example LXVI are stirred in 350 ml of concentrated aqueous hydrochloric acid at 100° C. for 2 hours (evolution of carbon dioxide) [compare R. A. Glennon and M. von Strandtmann, J. Heterocycl. Chem. 12, 135 (1975)]. The reaction mixture is evaporated to dryness and extracted by stirring with a mixed solvent ethanol:diethyl ether=1:1. The 1st precipitate is filtered off with suction, and the filtrate is extracted by stirring as before but now with a smaller amount of solvent, and again filtered with suction (2nd precipitate). The batches of product are dried over phosphorus pentoxide under high vacuum.

Yield:
1st precipitate: 19.96 g (118 mmol) 81% of theory.
2nd precipitate: 2.28 g (14 mmol) 9% of theory.
TLC: $R_f$=0.33 (BABA).
$^1$H-NMR (d$_6$-DMSO, 300 MHz, TMS): δ=4.19 (s, 2H); 7.13 (m, 1H); 7.2 (m, 1H); 7.31 (m, 1H); 7.42 (m, 1H); 9.95 (s, br, 1H); 10.17 (s, br, 1H); 12.39 (s, br, 1H) ppm.

EXAMPLE LXVIII
2-Nitro-5-chlorobenzyl cyanide

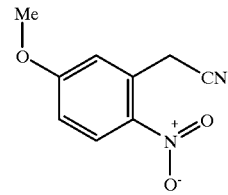

20 g(0.13 mol) of p-chloronitrobenzene in 125 ml of ether and 25 g(0.65 mol) of powdered sodium hydroxide are added to 300 ml of liquid ammonia with stirring. After stirring at about −35° C. for 10 min, 10.5 g (0.14 mol) of chloroacetonitrile in 25 ml of ether are added dropwise over the course of 40 min to this suspension at this temperature. After 2.5 h, the reaction is stopped by adding 25 g of solid ammonium chloride, the ammonia is evaporated off and the volume is kept approximately constant by adding tetrachloromethane. The ether is then substantially removed by distillation, and the reaction mixture is filtered hot. The residue is extracted twice with 300 ml of hot tetrachloromethane each time, and the combined filtrates are concentrated. This residue is extracted three times with 125 ml of hot cyclohexane each time, and the residue is purified by chromatography on silica gel.

Yield: 5 g (20%, Lit. 75%).
$R_f$=0.32 (petroleum ether:ethyl acetate 10:1).
$^1$H-NMR (200 MHz, CDCl$_3$): δ=4.22 (s, 2H); 7.56 (dd, 1H); 7.76 (d, 1H); 8.19 (d, 1H) ppm.
MS (CI, NH$_3$): 214 ([M+NH$_4$]$^+$, 100%).

EXAMPLE LXIX
2-Nitro-5-methoxybenzyl cyanide 44.0 g (0.167 mol) of the compound from Example LXIV are stirred in 450 ml of 1 N sodium carbonate solution at 50° C. for 18 h. After cooling to room temperature, the precipitate is filtered off with suction and dried at 50° C. in vacuo (0.1 torr).

Yield: 21.6 g (67%).
Melting point: 78° C.
$^1$H-NMR (200 MHz, CDCl$_3$): δ=3.95 (s, 3H); 4.26 (s, 2H); 6.98 (dd, 1H); 7.18 (d, 1H), 8.27 (d, 1H) ppm.
MS (CI, NH$_3$): 210 ([M+NH$_4$]$^+$, 100%).

The compounds in Table VI are prepared in analogy to the method in Example LXIX:

TABLE VI

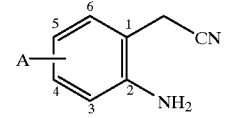

| Ex. No. | A | a) m.p. (° C.)<br>b) $R_f$ (solvent) | Spectra | Starting material from Ex. No. |
|---|---|---|---|---|
| LXX | 4-Cl | | MS (CI, NH$_3$): 214 ([M + NH$_4$]$^+$; 100%) | LXIII |
| LXXI | 4-OMe | a) 62° C. | | LXV |

EXAMPLE LXXII

2-Amino-5-chlorobenzyl cyanide

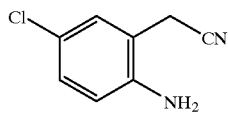

5.0 g (0.025 mol) of the compound from Example LXVIII and 4.6 g (0.039 mol) of tin are suspended in 40 ml of isopropanol and, at 10° C. under argon, 21 ml of concentrated hydrochloric acid are slowly added. After the addition is complete, the cooling bath is removed so that the internal temperature reaches 35–40° C. The tin has virtually dissolved after about 1.5 h, and addition of 1 N sodium hydroxide solution to a sample of the reaction solution no longer causes a blue coloration. The reaction mixture is concentrated to about 15 ml and filtered, the residue is dissolved in 50 ml of water and again filtered. The filtrate is adjusted to pH 8.0 at 5° C. with about 12 ml of 30% strength sodium hydroxide solution, and the precipitate is filtered off and washed twice with 25 ml of water each time. The filter cake is then extracted three times with 25 ml of boiling isopropanol each time, and the filtrate is concentrated in vacuo and dried.

Yield: 2.5 g (60%).

$^1$H-NMR (200 MHz, CDCl$_3$): δ=3.55 (s, 2H); 3.70 (s, broad, 2H); 6.69 (d, 1H); 7.14 (dd, 1H); 7.21 (d, 1H) ppm.

MS (EI): 166 (M$^+$, 74%).

The compounds in Table VII are prepared in analogy to the method in Example LXXII:

TABLE VII

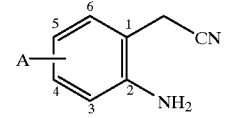

| Ex. No. | A | a) m.p. (° C.)<br>b) $R_f$ (solvent) | Spectra | Starting material from Ex. No. |
|---|---|---|---|---|
| LXXIII | 4-Cl | a) 85° C. | | LXX |
| LXXIV | 5-OMe | | MS (CI, NH$_3$): 163 ([M + H]$^+$, 100%) | LXIX |
| LXXV | 4-OMe | | MS (CI, NH$_3$): 163 ([M + H]$^+$, 100%) | LXXI |

EXAMPLE LXXVI

2-Amino-5-chloroindole hydrochloride

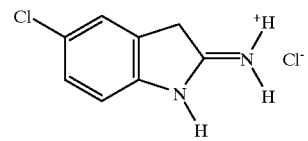

1.2 g (0.053 mol) of sodium are dissolved in 30 ml of isopropanol. To this solution at about 80° C. are added 2.5 g (0.015 mol) of the compound from Example No. LXXII in 15 ml of isopropanol, and the mixture is then boiled under reflux for 1.5 h. 15 ml of water are added to the reaction solution at 60° C., the isopropanol is substantially removed in vacuo, and the precipitate is filtered off. The latter is then taken up in 12 ml of isopropanol, 1 ml of water is added, and the pH is adjusted to 2.0 with ethanolic hydrochloric acid. Renewed concentration is followed by recrystallization from water/acetone and drying in vacuo.

Yield: 1.6 g (53%).

$^1$H-NMR (200 MHz, CDCl$_3$): δ=4.22 (s, 2H); 7.24 (d, 1H); 7.37 (d, 1H); 7.51 (d, 1H); 10.18 (s, 1H); 10.40 (s, 1H); 12.58 (s, 1H) ppm.

MS (EI): 166 (M$^+$, 100%).

The compounds in Table VIII are prepared in analogy to the method in Example No. LXXVI:

TABLE VIII

| Ex. No. | A | a) m.p. (° C.)<br>b) $R_f$ (solvent) | Spectra | Starting material from Ex. No. |
|---|---|---|---|---|
| LXXVII | 6-Cl | a) >200° C. | MS (CI, NH$_3$): 167 ([M + H]$^+$, 100%) | LXXIII |
| LXXVIII | 5-OMe | a) >200° C. | MS (CI, NH$_3$): 163 ([M + H]$^+$, 100%) | LXXIV |
| LXXIX | 6-OMe | a) >200° C. | MS (CI, NH$_3$): 163 ([M + H]$^+$, 100%) | LXXV |

EXAMPLE LXXX 2,4-Dimethylpyrimido[1,2-d]indole

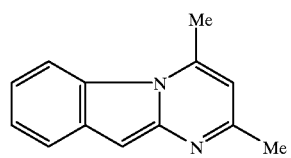

22 g (131 mmol) of the compound from Example LXVII in 200 ml of pyridine are reacted with 16.7 ml (196 mmol) of 2,4-pentanedione at about 20° C. [compare A. N. Kost, R. S. Sagitullin, V. I. Gorbunov and N. N. Modyanov, Khim. Geterosikl. Soedin 6, 359–363 (1970); English translation 334–337]. After 20 hours, the reaction mixture is poured into 1.2 l of water and the resulting precipitate is filtered off with suction. The crude solid is washed several times with water, sucked dry and dried over phosphorus pentoxide under high vacuum.

Yield: 22.5 g (115 mmol) 88% of theory.
TLC: $R_f$=0.31 (B).
$^1$H-NMR (CDCl$_3$, 300 MHz, TMS): δ=2.51 (s, 3H); 2.93 (s, 3H); 6.19 (s, 1H); 6.77 (s, 1H); 7.25 (m, 1H); 7.38 (m, lH); 7.83 (m, 1H); 8.05 (m, 1H) ppm.

The compounds in Table IX are prepared in analogy to the method in Example LXXX:

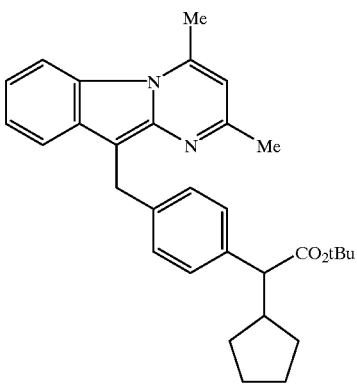

6.57 g (33.5 mmol) of the compound from Example LXXX, 26.1 g (50.2 mmol) of the compound from Example XXXII and 10.9 g (33.46 mmol) of caesium carbonate are mixed in 70 ml of anhydrous N,N-dimethylformamide under argon at about 20° C. and stirred in an oil bath at 120° C. for 45 minutes. The cooled reaction mixture is poured into cold water and extracted with diethyl ether. The organic phase is dried with magnesium sulphate and evaporated. The crude product obtained in this way is extracted by stirring with methanol, filtered off with suction, washed with methanol and dried over phosphorus pentoxide under high vacuum.

1st yield: 8.02 g (17.1 mmol) 51% of theory

The evaporated filtrate is purified by chromatography on silica gel 60 (Merck/40–63 μm/petroleum ether:ethylacetate=10:1 to 5:1).

2nd yield: 1.40 g (3.0 mmol) 9% of theory.
TLC: $R_f$=0.44 (C).
$^1$H-NMR (CDCl$_3$, 200 MHz, TMS) δ=0.93 (m, 1H); 1.36 (s, 9H); 1.14–1.71 (m, 6H); 1.85 (m, 1H); 2.38 (m, 1H); 2.51

TABLE IX

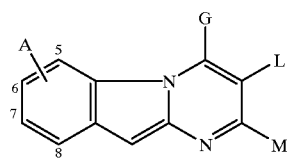

| Ex. No. | A | G | L | M | a) m.p. (° C.) b) $R_f$ (solvent) | Spectra | Starting material from Ex. No. |
|---|---|---|---|---|---|---|---|
| LXXXI | H | Me | H | Et | b) 0.39 (L) | | LXVII |
| LXXXII | H | Et | H | Me | b) 0.31 (L) | | LXVII |
| LXXXIII | H | Et | H | Et | | MS (CI): 224 (M$^+$. 100%) | LXVII |
| LXXXIV | H | Me | Me | Me | b) 0.60 (B) | | LXVII |
| LXXXV | H | Me | Et | Me | b) 0.48 (B) | | LXVII |
| LXXXVI | H | Et | Me | Me | b) 0.75 (B) | | LXVII |
| LXXXVII | H | Me | Me | Et | b) 0.60 (B) | | LXVII |
| LXXXVIII | 6-Cl | Me | H | Me | a) 155° C. | | LXXVI |
| LXXXIX | 7-Cl | Me | H | Me | | MS (CI, NH$_3$): 231 ([M + H]$^+$:- 100%) | LXXVII |
| XC | 6-OMe | Me | H | Me | b) 0.85 (I) | | LXXVIII |
| XCI | 7-OMe | Me | H | Me | a) 76° C. | | LXXIX |

EXAMPLE XCII tert-Butyl 2(R/S)-cyclopentyl-2-[4-(2,4-dimethyl-pyrimido [1,2-a]indol-9-yl-methyl)phenyl]acetate (s, 3H); 2.92 (s, 3H); 3.06 (d, 1H); 4.46 (s, 2H); 6.15 (s, 1H); 7.12–7.34 (m, 6H); 7.63 (m, 1H), 8.05 (m, 1H) ppm.

The racemic compounds in Table X are prepared in analogy to the method in Example XCII:

TABLE X

| Ex. No. | A | G | L | M | X | Y | a) m.p. (° C.) b) R_f (solvent) | Spectra | Starting material from Ex. No. |
|---|---|---|---|---|---|---|---|---|---|
| XCIII | H | Me | H | Me | H | tBu | b) 0.63 (J) | | LXXX and XXXIV |
| XCIV | H | Me | H | Me | Me | tBu | b) 0.28 (C) | | LXXX and XXXV |
| XCV | H | Me | H | Me | Et | tBu | b) 0.34 (C) | | LXXX and XXXVI |
| XCVI | H | Me | H | Me | nPr | tBu | b) 0.49 (C) | | LXXX and XXXVII |
| XCVII | H | Me | H | Me | nBu | tBu | b) 0.35 (C) | | LXXX and XL |
| XCVIII | H | Me | H | Me | iBu | tBu | b) 0.57 (B) | | LXXX and XLI |
| IC | H | Me | H | Me | nPent | tBu | | MS(CI, NH$_3$): 431 ([M + H]$^+$), 100%) | LXXX and XLII |
| C | H | Me | H | Me | iPent | tBu | b) 0.54 (J) | | LXXX and XLIII0 |
| CI | H | Me | H | Me | —CH(Et)$_2$ | tBu | b) 0.69 (J) | | LXXX and XLIV |
| CII | H | Me | H | Me | nHex | tBu | b) 0.36 (C) | | LXXX and XLV |
| CIII | H | Me | H | Me | —CH$_2$CH(Et)$_2$ | tBu | b) 0.69 (J) | | LXXX and XLVI |
| CIV | H | Me | H | Me | cHex | tBu | b) 0.27 (C) | | LXXX and IL |
| CV | H | Me | H | Me | cHex | Me | b) 0.51 (C) | | LXXX and XLVIII |
| CVI | H | Me | H | Me | cHept | tBu | b) 0.48 (C) | | LXXX and LI |
| CVII | H | Me | H | Me | cOct | tBu | b) 0.25 (C) | | LXXX and LII |
| CVIII | H | Me | H | Me | —CH$_2$-cPent | tBu | b) 0.42 (C) | | LXXX and LIII |
| CIX | H | Me | H | Me | —⟨C$_6$H$_4$⟩-Cl | Me | b) 0.43 (J) | | LXXX and |
| CX | H | Me | H | Et | cPent | tBu | b) 0.37 (H) | | LXXXI and XXXII |
| CXI | H | Et | H | Me | cPent | tBu | b) 0.82 (L) | | LXXXII and XXXII |
| CXII | H | Et | H | Et | cPent | tBu | b) 0.70 (B) | | LXXXIII and XXXII |
| CXIII | H | Me | Me | Me | cPent | tBu | b) 0.47 (K) | | IXXXIV and XXXII |
| CXIV | H | Me | Et | Me | cPent | Ment | b) 0.50 (C) | | LXXXV and CLXXII |
| CXV | H | Et | Me | Me | cPent | Ment | b) 0.54 (C) | | LXXXVI and CLXXII |
| CXVI | H | Me | Me | Et | cPent | Ment | b) 0.50 (C) | | LXXXVI and CLXXII |
| CXVII | 6-Cl | Me | H | Me | cPent | tBu | a) 181° C. | | LXXXVIII and XXXII |
| CXVIII | 7-Cl | Me | H | Me | cPent | tBu | | MS (CI, NH$_3$), 503 (M$^+$, 100%) | LXXXIX and XXXII |

TABLE X-continued

[Structure with substituents A, G, L, M, X, Y shown on pyrimido-indole core with phenyl-acetate]

| Ex. No. | A | G | L | M | X | Y | a) m.p. (° C.) b) R_f (solvent) | Spectra | Starting material from Ex. No. |
|---|---|---|---|---|---|---|---|---|---|
| CXIX | 6-OMe | Me | H | Me | cPent | tBu | b) 0.87 (L) | | XC and XXXII |
| CXX | 7-OMe | Me | H | Me | cPent | tBu | b) 0.84 (L) | | XCI and XXXII |

EXAMPLE CXXI
2(R/S)-2-Cyclopentyl-2-[4-(2,4-dimethyl-pyrimido[1,2-a]indol-9-yl-methyl)phenyl]-acetic acid

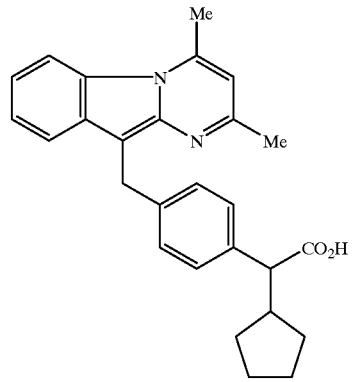

8.00 g (17.1 mmol) of the compound from Example XCII are reacted with 14 ml of concentrated hydrochloric acid in 60 ml of dioxane at a bath temperature of 70° C. for 1.5 h. The reaction solution is cooled and diluted with 600 ml of water, and the pH is adjusted to 2.5 with 2 M aqueous sodium hydroxide solution. The precipitate resulting from this is filtered off with suction, washed several times with water and dried over phosphorus pentoxide under high vacuum.

Yield: 6.89 g (16.7 mmol) 98% of theory.

TLC: $R_f$=0.41 (D).

$^1$H-NMR (D$_6$-DMSO, 200 MHz, TMS): δ=0.89 (m, 1H); 1.08–1.61 (m, 6H); 1.78 (m, 1H); 2.37 (m, 1H); 2.46 (s, 3H); 2.96 (s, 3H); 4.32 (s, 2H); 6.46 (s, 1H); 7.11–7.37 (m, 6H); 7.70 (m, 1H); 8.19 (m, 1H); 12.15 (s, br, 1H) ppm.

The racemic compounds in Table XI are prepared in analogy to the method in Example CXXI:

TABLE XI

[Structure with substituents A, G, L, M, X shown on pyrimido-indole core with phenyl-acetic acid]

| Ex. No. | A | G | L | M | X | a) m.p.(° C.) b) R_f (solvent) | Spectra | Starting material from Ex. No. |
|---|---|---|---|---|---|---|---|---|
| CXXII | H | Me | H | Me | H | | MS (CI, NH$_3$): 345 ([M + H]$^+$, 20%) | XCIII |
| CXXIII | H | Me | H | Me | Me | b) 0,23 (D) | | XCIV |

TABLE XI-continued

[Structure diagram of substituted pyrimido[1,2-a]indole with substituents A, G, L, M, X on core scaffold bearing phenyl-acetic acid group]

| Ex. No. | A | G | L | M | X | a) m.p.(° C.) b) R_f (solvent) | Spectra | Starting material from Ex. No. |
|---|---|---|---|---|---|---|---|---|
| CXXIV | H | Me | H | Me | Et | b) 0,38 (D) | | XCV |
| CXXV | H | Me | H | Me | nPr | b) 0,29 (D) | | XCVI |
| CXXVI | H | Me | H | Me | nBu | b) 0,17 (B) | | XCVII |
| CXXVII | H | Me | H | Me | iBu | b) 0,25 (B) | | XCVIII |
| CXXVIII | H | Me | H | Me | nPent | | MS (CI, NH$_3$): 415 ([M + H]$^+$- 100%) | IC |
| CXXIX | H | Me | H | Me | iPent | | MS (CI, NH$_3$): 414 (M$^+$, 100%) | C |
| CXXX | H | Me | H | Me | CH(Et)$_2$ | | MS (CI, NH$_3$): 415 ([M + H]$^+$, 100% | CI |
| CXXXI | H | Me | H | Me | nHex | b) 0.20 (B) | | CII |
| CXXXII | H | Me | H | Me | —CH$_2$CH(Et)$_2$ | | MS (CI, NH$_3$): 429 ([M + H]$^+$, 100%) | CIII |
| CXXXIII | H | Me | H | Me | cHex | b) 0.16 (B) | | CIV |
| CXXXIV | H | Me | H | Me | cHept | b) 0.52 (D) | | CVI |
| CXXXV | H | Me | H | Me | cOct | b) 0,45 (D) | | CVII |
| CXXXVI | H | Me | H | Me | —CH$_2$cPent | b) 0,22 (D) | | CVIII |
| CXXXVII | H | Me | H | Et | cPent | b) 0.13 (L) | | CX |
| CXXXVIII | H | Et | H | Me | cPent | h) 0.26 (L) | | CXI |
| CXXXIX | H | Et | H | Et | cPent | | MS (CI, NH$_3$) 441 ([M + H]$^+$, 100% | CXII |
| CXL | H | Me | Me | Me | cPent | | MS (CI, NH$_3$) 427 ([M + H]$^+$, 100% | CXIII |
| CXLI | 6-Cl | Me | H | Me | cPent | | MS (CI, NH$_3$) 447 ([M + H]$^+$, 100% | CXVII |
| CXLII | 7-Cl | Me | H | Me | cPent | | MS (CI, NH$_3$) 447 ([M + H]$^+$,100% | CXVIII |
| CXLIII | 6-OMe | Me | H | Me | cPent | | MS (CI, NH$_3$) 443 ([M + H]$^+$, 100% | CXIX |
| CXLIV | 7-OMe | Me | H | Me | cPent | | MS (CI, NH$_3$) 442 (M$^+$, 100% | CXX |

EXAMPLE CXLV 2-(S)-2-Cyclopentyl-2-[4-{(2,4-dimethyl-3-ethyl-pyrimido[1,2-a]indol-9-yl)methyl}phenyl-acetic acid

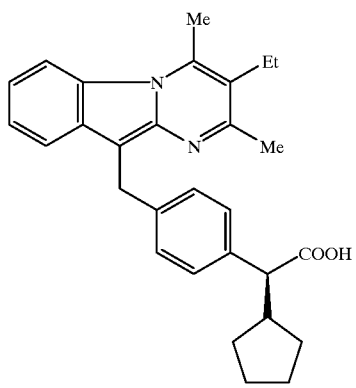

445 mg (0.769 mmol) of the compound from Example CXIV are boiled under reflux in 6 ml of formic acid and 3 ml of 48% strength hydrobromic acid for 4 h, then poured into water and adjusted to pH=2 with sodium bicarbonate. The resulting precipitate is filtered off with suction, washed with water, sucked dry, washed with petroleum ether and again sucked dry. The crude yield after drying over phosphorus pentoxide in vacuo is 242 mg. The mother liquor from this work-up is taken up in diethyl ether and water, the aqueous phase is back-extracted with ether, the combined organic phases are dried with anhydrous magnesium sulphate, and the solvent is removed in vacuo—finally under high vacuum.

Crude yield: 50 mg

The combined batches of product are purified by chromatography in silica gel 60 (Merck/dichloromethane:ethanol=100:1).

Yield: 259 mg.

R$_f$=0.30 (B).

The compounds in Table XII are prepared in analogy to the method in Example CXLV:

TABLE XII

[Structure with substituents A, G, L, M, X on pyrimido[1,2-a]indole core with phenylacetic acid group]

| Ex. No. | A | G | L | M | X | a) m.p. (° C.) b) $R_f$ (solvent) | Spectra | Starting material from Ex. No. |
|---|---|---|---|---|---|---|---|---|
| CXLVI | H | Et | Me | Me | cPent | b) 0.27 (B) | | CXV |
| CXLVII | H | Me | Me | Et | cPent | b) 0.18 (B) | | CXVI |

EXAMPLE CXLVIII

2(R/S)-2-Cyclopentyl-2-[4-{(2,4-dimethyl-pyrimido[1,2-a]indol-9-yl)methyl}-phenyl]-acetic acid 4.16 g (9.45 mmol) of the compound from Example CV are reacted in 132 ml of 1 M aqueous sodium hydroxide solution and 200 ml of 1,4-dioxane at 60° C. for 72 h. The reaction mixture is evaporated to about 150 ml, 400 ml of water are added, and the pH is adjusted to 2.5 at 0° C. with 2 M aqueous hydrochloric acid. The precipitate resulting from this is filtered off with suction, washed with water, sucked dry and dried over phosphorus pentoxide in vacuo.

Yield: 3.5 g.

$R_f$=0.20 (B).

The racemic compounds in Table XIII are prepared in analogy to the method in Example CXLVIII:

TABLE XIII

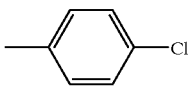

| Ex. No. | A | G | L | M | X | a) m.p.(° C.) b) $R_f$ (solvent) | Spectra | Starting material from Ex. No. |
|---|---|---|---|---|---|---|---|---|
| CIL | H | Me | H | Me | —⟨4-C6H4-Cl⟩ | b) 0.27 (I) | | CIX |

The compounds in Table XIV are prepared in analogy to the method in Example XCII:

TABLE XIV

[Structure: indole fused with pyrimidine bearing Me groups, with CH2-phenyl-X-C(=O)-O-tBu substituent]

| Ex. No. | —X— | a) m.p. (° C.) b) R_f (solvent) | Spectra | Starting material from Ex. No. |
|---|---|---|---|---|
| CL | \C(Me)2/ | b) 0.42 (G) | | LXXX and LV |
| CLI | \C(Et)2/ | b) 0.13 (A) | | LXXX and LVI |
| CLII | \C(nPr)2/ | b) 0,34 (C) | | LXXX and LVII |
| CLIII | \C(nBu)2/ | b) 0.36 (C) | | LXXX and LVIII |
| CLIV | cyclopentyl | b) 0.75 (J) | | LXXX and LIX |

TABLE XIV-continued

| Ex. No. | —X— | a) m.p. (° C.) b) R_f (solvent) | Spectra | Starting material from Ex. No. |
|---|---|---|---|---|
| CLV | cyclohexyl | b) 0.56 (J) | | LXXX and LX |
| CLVI | cycloheptyl | b) 0.37 (K) | | LXXX and LXI |

The compounds in Table XV are prepared in analogy to the method in Example CXXI:

TABLE XV

[Structure: indole fused with pyrimidine bearing Me groups, with CH2-phenyl-X-C(=O)-OH substituent]

| Ex. No. | —X— | a) m.p. (° C.) b) R_f (solvent) | Spectra | Starting material from Ex. No. |
|---|---|---|---|---|
| CLVII | \C(Me)2/ | b) 0.11 (B) | | CL |

TABLE XV-continued

| Ex. No. | —X— | a) m.p. (° C.)<br>b) $R_f$ (solvent) | Spectra | Starting material from Ex. No. |
|---|---|---|---|---|
| CLVIII | C(Et)$_2$ | | MS (CI, NH$_3$): 401<br>([M + H]$^+$, 100%) | CLI |
| CLIX | C(nPr)$_2$ | b) 0.20 (B) | | CLII |
| CLX | C(nBu)$_2$ | b) 0.25 (B) | | CLIII |
| CLXI |  | | MS (FAB): 399<br>([M + H]$^+$, 15%) | CLIV |
| CLXII |  | | MS (FAB): 412<br>(M$^+$, 100%) | CLV |
| CLXIII |  | | MS (CI, NH$_3$): 427<br>([M + H]$^+$, 100%) | CLVI |

EXAMPLE CLXIV

Methyl 2(R/S)-2-cyclopentyl-2-(3-tolyl)acetate

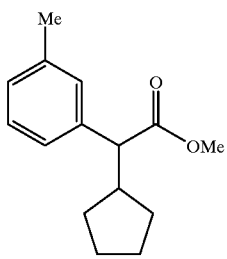

The title compound is prepared in analogy to the method in Example IV from methyl 2-(3-tolyl)acetate.

$R_f$=0.56 (P).

EXAMPLE CLXV

Methyl 2(R/S)-2-(3-bromomethylphenyl)-2-cyclopentylacetate

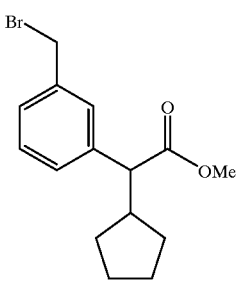

The title compound is prepared in analogy to the method for Example XXXII from the compound of Example CLXIV.

$R_f$=0.40 (P).

EXAMPLE CLXVI
2(R/S)-2-Cyclopentyl-2-(4-methylphenyl)-acetic acid

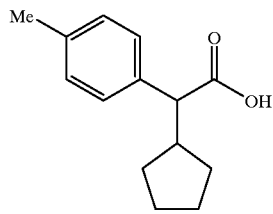

2.0 kg (7.2 mol) of the compound from Example IV are dissolved in 4 l of dioxane in a 40 l vessel with stirrer and connected washtower. Addition of 4.5 l of concentrated hydrochloric acid is followed by stirring at 50° C. until conversion is complete (3 h). Ice is added to the reaction mixture, and the pH is adjusted to 12 with concentrated sodium hydroxide solution. Addition of water to dissolve the solids completely is followed by washing with acetic acid, the organic phase is washed with dilute sodium hydroxide solution, and the combined aqueous phases are adjusted to pH=1 with concentrated hydrochloric acid while cooling. Two washes with ethyl acetate are followed by drying over sodium sulphate and concentration.

Yield: 1.27 kg, 81% of theory.
Melting point: 92° C.
$R_f$=0.20 (petroleum ether: ethyl acetate=4:1).
$^1$H-NMR (CDCl$_3$, 200 MHz, TMS): δ=0.98 (m, 1H); 1.20–1.71 (m, 6H); 1.82–2.05 (m, 1H); 2.31 (s, 3H); 2.52 (m, 1H); 3.21 (d, 1H); 7.10 (m, 2H); 7.21 m, 2H); 11.90 (br, s, 1H) ppm.

EXAMPLE CLXVII
(S)-(+)-2-Cyclopentyl-2-(4-methylphenyl)-acetic acid

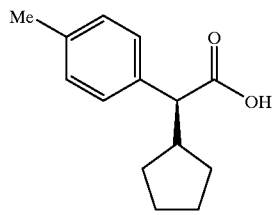

2.4 l of THF and 129.7 g (1.28 mol) of triethylamine are added with stirring to a suspension of 560 g (2.57 mol) of the compound from Example CLXVI in 4.8 l of water. The resulting solution is heated to 60° C., 155.4 g (1.28 mol) of (S)-(−)-phenethylamine are added, and the resulting suspension is stirred at 60° C. for 2 h. The reaction mixture is cooled to 20° C., and the precipitate is filtered off with suction, washed with 2.4 l of water/THF (2:1) and dried in vacuo.

Yield: 360 g of phenethylammonium salt; 41.3% of theory based on racemate of Example No. CLXVI 745 g (2.2 mol) of phenethylammonium salt are suspended in 3 l of water, acidified (pH=1) with dilute hydrochloric acid (1:1) and stirred for 30 minutes. The oily suspension is washed three times with 1 l of dichloromethane each time, and the combined organic phases are washed with water, dried over sodium sulphate and concentrated, whereupon the residue crystallizes.

Yield: 475 g, 37.3% of theory based on racemate of Example No. CLXVI.

ee: 96.3% (HPLC).

Melting point: 66° C.

The pure enantiomer is obtained by crystallization of the phenethylammonium salt from THF and liberation of Example No. CLXVII as described above:

ee:>99.5% (HPLC)

Optical rotation: $[\alpha]_D^{20}$=+59.55 (ethanol/c=0.85)

The HPLC method for determining the ee is as follows (the racemic compound from Example CLXVI is used for comparison):

Column: Chiracel OJ (Daicel),
Particle size: 10μ,
Packing: 250×2 mm (from Grom).
Mobile phase: n-heptane: 2-propanol=97:3.
Flow rate: 0.2 ml/min,
Inlet pressure: 22 bar.

EXAMPLE CLXVIII
tert-Butyl (S)-(+)-2-cyclopentyl-2-(4-methylphenyl)acetate

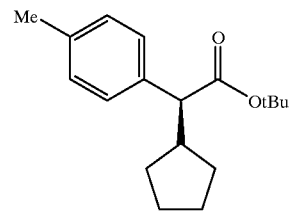

6 ml of concentrated sulphuric acid are added to a solution of 465 g (2.13 mol) of the compound from Example CLXVII in 1.4 l of dichloromethane, whereupon the temperature settles at about 10° C. 550 ml (5 mol) of isobutene are condensed into a Dewar vessel and added in one portion to the precursor solution. The reaction mixture is stirred overnight. To complete the conversion, once again 6 ml of concentrated sulphuric acid and 500 ml of isobutene are added and stirred overnight. Addition of 40 g of potassium carbonate is followed by stirring for 3 h, and then 2 l of water are added, whereupon there is initially a large evolution of gas. After washing three times with 2 l of dichloromethane each time, the combined organic phases are washed with 5 l of sodium chloride solution, dried over sodium sulphate and concentrated to an oil, which slowly crystallizes.

Yield: 480 g, 82% of theory.

Melting point: 45° C.

$R_f$=0.90 (toluene:ethyl acetate=8:2).

EXAMPLE CLXIX tert-Butyl (S)-(+)-2-(4-bromomethylphenyl)-2-cyclopentylacetate

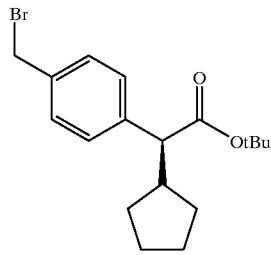

480 g (1.75 mol) of the compound from Example CLXVIII are dissolved in 3.4 l of tetrachloromethane under reflux in a 10 l flask, and 70 g of the total amount of 311 g(1.75 mol) of NBS, and 14 g(0.085 mol) of AIBN are added. The reaction starts after refluxing for about 1 h; after it has subsided, further NBS is added in 50 g portions. After refluxing for 5 h and subsequently standing at room temperature overnight, for work-up the mixture is cooled to 0° C., and the succinimide is filtered off with suction and washed with 600 ml of tetrachloromethane. The combined filtrates are concentrated, and residual solvent is removed to constant weight in vacuo.

Crude yield: 570 g, about 100% of theory.

HPLC: 68.8% (15.5% precursor, 10.1% dibromo compound).

The pure substance is obtained by column chromatography.

$R_f$=0.42 (Q).

$^1$H-NMR (CDCl$_3$, 200 MHz, TMS): δ=0.98 (m, 1H); 1.22–1.71 (m, 6H); 1.40 (s, 9H); 1.90 (m, 1H); 2.47 (m, 1H); 3.16 (d, 1H); 4.49 (s, 2H); 7.32 (m, 4H) ppm.

EXAMPLE CLXX (L)-Menthyl 2-(4-tolyl)acetate

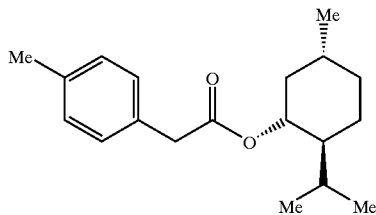

3.15 kg of p-tolylacetic acid are introduced into 9.45 l of toluene. While stirring and cooling, 3.115 kg of L-menthol and 21.4 ml of methanesulphonic acid are added. The mixture is then heated to reflux temperature and the appropriate amount of water is removed in a water trap over the course of 16 to 20 hours. Cooling to room temperature is followed by extraction by stirring once with 4.41 l of saturated sodium bicarbonate solution and twice with 4.41 l of water each time. The solvent is removed from the organic phase to afford 5.725 kg of required compound (GC 99.9%, retention time 19.49 min).

$^1$H-NMR (CDCl$_3$, ppm): 7.05–7.15 (4H, m); 4.55 (1H, txd); 3.5 (2H, s); 2.8 (3H, s); 0.65 (3H, s).

EXAMPLE CLXXI (L)-Menthyl 2-(S)-2-cyclopentyl-2-(4-tolyl)acetate

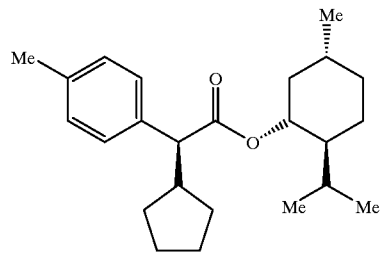

1.575 kg of potassium tert-butanolate are dissolved in 3.75 l of DMF at room temperature. The solution is cooled to 10° C. and, at this temperature, 2.678 kg of the compound from Example CLXX are run in over the course of 45 minutes, washing with 0.375 l of DMF. Then, cooling fully, 1.658 kg of cyclopentyl bromide are pumped in over the course of 1 to 2 hours. The suspension is stirred for a further hour without cooling and then cooled to −7° C. When −10° C. is reached, seeding is carried out with the correct diastereomer, and cooling at −7° C. is continued. After −7° C. is reached, the mixture is stirred at this temperature for 3 to 4 hours. Work-up takes place by introducing the reaction suspension into a mixture of 1.5 kg of ice and 6 kg of water. The mixture is then stirred at 0 to 2° C. overnight. Work-up takes place by filtering the suspension with suction and washing the crystals with a total of 2.5 l of water. The crystals are dried in a vacuum oven at 45° C. 3.289 kg of an 85:15 diastereomer mixture are obtained.

4.345 kg of a mixture prepared as described above are dissolved in 21.75 l of methanol at 30 to 35° C. After seeding with the correct diastereomer and cooling to room temperature, the mixture is stirred overnight and cooled to 0 to 5° C. the next morning. After 1 to 2 hours at this temperature, the crystals are filtered off with suction, dried or again recrystallized. Repetition of the methanol crystallization once or twice allows material with a diastereomeric purity ≧99.5% to be prepared (GC retention time 22.61 min).

The yield of diastereomerically pure title compound is 65–70% over the cyclopentylation and purification by crystallization stages and can be increased to 75–80% by recrystallization or by epimerization of the mother liquors with potassium tert-butanolate in DMF and renewed crystallization of the crude diastereomer mixture.

$^{13}$C-NMR (CDCl$_3$, CH signals, ppm) 128.90; 128.92; 73.96; 57.85; 46.92; 43.13; 31.28; 25.96 ppm.

EXAMPLE CLXXII (L)-Menthyl 2-(S)-2-(4-bromomethylphenyl)-2-cyclopentylacetate

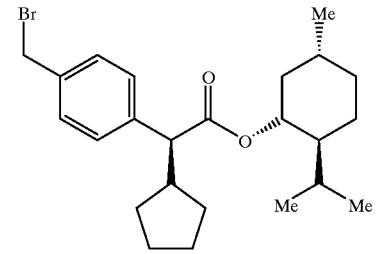

1.40 kg of the compound from Example CLXXI in 13.74 l of chlorobenzene are heated to 80° C. Then 0.618 kg of 1,3-dibromo-5,5-dimethylhydantoin is added, and the mixture is further heated to 85° C. Then, at this temperature, 20.4 g of AIBN are added to start the reaction. After the reaction has started, the temperature rises to 90 to 105° C., but then falls back to about 85° C. Reaction is continued for a total of 2 hours. The contents of the vessel are then cooled to room temperature and stirred for one hour. The precipitated crystals are filtered off with suction, and the solvent is removed from the filtrate. The remaining oil is 61.2% pure according to HPLC analysis (retention time 14.68 min.). 1.69 kg are obtained. The crude mixture can be employed in the following alkylations. Chromatography and subsequent crystallization afford a white powder of melting point 57–58° C. with correct CH analysis.

$^1$H-NMR (CDCl$_3$, ppm): 7.3 (4H, s); 4.65 (1H, txd); 4.45 (2H, s); 3.35 (1H, d); 0.65 (3H, d).

EXAMPLE CLXXIII
Methyl 2-(R/S)-2-phenyl-2-(4-methylphenyl)acetate

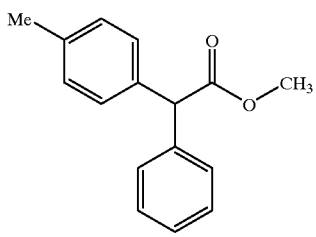

21.0 g (100 mmol) of 2-phenyl-1-(4-methylphenyl)-1-oxoethane and 38.8 g (120 mmol) of iodobenzene diacetate are dissolved in 300 ml of trimethyl orthoformate. 19.6 g of concentrated sulphuric acid are added to this solution, and the solution is stirred at 60° C. for 6 h. The solution is cooled to room temperature, diluted with water and extracted with diethyl ether. The combined organic phases are dried over sodium sulphate and evaporated in a rotary evaporator. The residue is purified by column chromatography.

Yield: 13.1 g (55%).

R$_f$=0.33 (Q).

MS (FAB): 241 (25%), 181 (100%).

$^1$H-NMR (200 MHz, CDCl$_3$, TMS): δ=7.3–7.10 (m, 9H); 4.99 (s, 1H); 3.73 (s, 3H); 2.31 (s, 3H) ppm.

EXAMPLE CLXXIV
Methyl 2-(R/S)-2-(4-chlorophenyl)-2-(4-tolyl)acetate

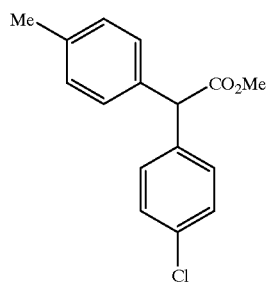

The title compound is prepared in analogy to the method in Example CLXXIII.

R$_f$=0.41 (Q).

The racemic compounds in Table XVI are prepared in analogy to the method in Example XXXII:

TABLE XVI

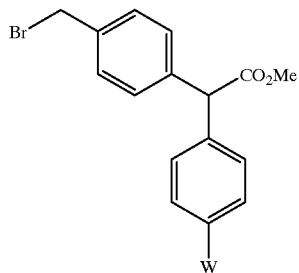

| Ex. No. | W | a) m.p. (° C.)<br>b) R$_f$ (solvent) | Spectra | Starting material from Ex. No. |
|---|---|---|---|---|
| CLXXV | H | b) 0.74 (G) | | CLXXIII |
| CLXXVI | Cl | b) 0.28 (G) | | CLXXIV |

Preparation Examples

Example 1
N-{2(R)- and 2(S)-2-Cyclopentyl-2-[4-(2,4-dimethyl-pyrimido[1,2-a]indol-9-yl-methyl)phenyl]acetyl}-(R)-phenylglycinol

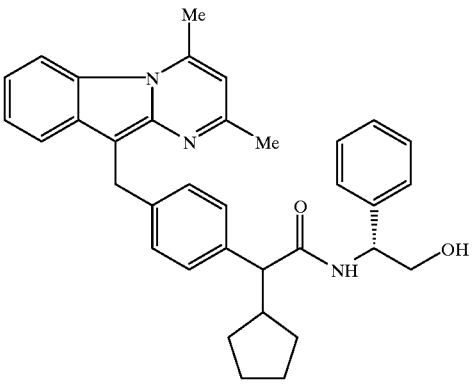

1.88 g (4.56 mmol) of the compound from Example CXXII are reacted in 20 ml of dichloromethane with 0.63 g (4.56 mmol) of (R)-phenylglycinol, 0.68 g (5.00 mmol) of 1-hydroxy-1H-benzotriazole, 1.01 g (5.20 mmol) of N'-(3-dimethylaminopropyl)-N-ethylcarbodiimide hydrochloride and 1.27 g (9.12 mmol) of triethylamine at about 20° C. for 20 h. The reaction solution is then first washed with a buffer of pH=2, and thereafter dried with magnesium sulphate and evaporated. The crude diastereomer mixture is purified on silica gel 60 (Merck/40–63 μm/dichloromethane:ethanol= 20:1).

Yield: 2.20 g (4.14 mmol) 91% of theory

The isomers (Examples 2 and 3) are separated by chromatography.

452 mg of the yield described in Example 1 are dissolved in 10 ml of acetonitrile, 13 ml of methanol and 2 ml of water and the resulting solution is loaded onto the HPLC column in several injection steps.

Stationary phase: Kromasil 100 C18 5 μm.

Temperature: 50° C.

Flow rate: 20 ml/min

Mobile phase: acetonitrile:water:methanol=37.5:25:37.5.

The eluates are collected after UV detection (230 nm) and first evaporated in vacuo and then freeze-dried to remove residual solvent.

Diastereomer A (Example 2): 176 mg.
Diastereomer B (Example 3): 160 mg.

Example 2

N-{2(S)-2-Cyclopentyl-2-[4-(2,4-dimethyl-pyrimido[1,2-a]indol-9-yl-methyl)phenyl]-acetyl}-(R)-phenylglycinol

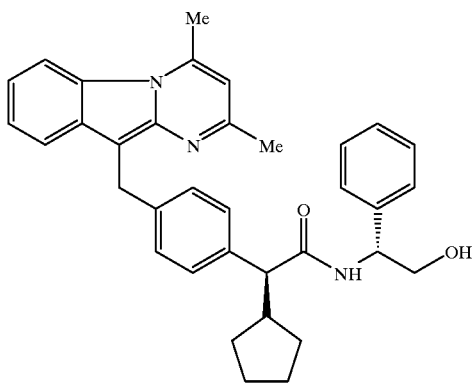

TLC: $R_f$=0.19 (petroleum ether:ethyl acetate=1:1).

Melting point: 208° C. (uncorrected).

$^1$H-NMR (CDCl$_3$, 300 MHz, TMS): δ=0.97 (m, 1H); 1.26 (m, 1H); 1.38–2.02 (m, 6H); 2.28 (m, 1H); 2.51 (s, 3H); 2.55 (m, 1H); 2.94 (s, 3H); 3.03 (d, 1H); 3.77–3.89 (m, 2H); 4.48 (s, 2H); 4.94 (m, 1H); 5.99 (d, 1H); 6.17 (s, 1H); 6.96–7.00 (m, 2H); 7.10–7.34 (m, 9H); 7.67 (m, 1H); 8.07 (m, 1H) ppm.

Example 3

N-{2(R)-2-Cyclopentyl-2-[4-(2,4-dimethyl-pyrimido[1,2-a]indol-9-ylmethyl)phenyl]acetyl}-(R)-phenylglycinol

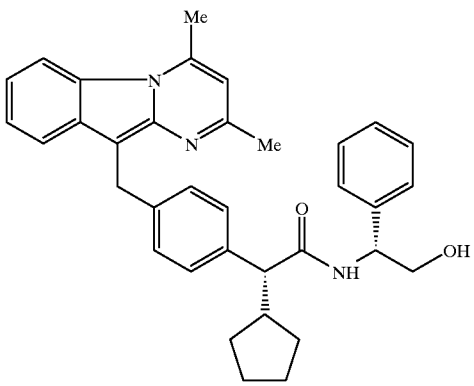

TLC: $R_f$=0.19 (petroleum ether:ethyl acetate=1:1).

Melting point: 191° C. (uncorrected).

$^1$H-NMR (CDCl$_3$, 200 MHz, TMS): δ=0.97 (m, 1H); 1.22 (m, 1H); 1.36–1.68 (m, 6H); 1.86 (m, 1H); 2.49 (m, 1H); 2.52 (s, 3H); 2.94 (s, 3H); 3.01 (d, 1H); 3.66–3.81 (m, 2H); 4.48 (s, 2H); 4.93 (m, 1H); 6.07 (d, 1H); 6.18 (s, 1H); 7.13–7.37 (m, 11H); 7.66 (m, 1H); 8.06 (m, 1H) ppm.

The absolute configuration of the enantiomerically pure carboxylic acids 2-(S)- and 2-(R)-2-{4-(2-quinolinylmethoxy)phenyl)}2-cyclopentylacetic acid [compare EP 509 359] are known so that the absolute configurations of the amides of Example No. C1 and Example No. C2 prepared therefrom in analogy to the method in Examples 1 and 2 can be deduced. The $^1$H-NMR spectra of the two diastereomeric products (200 MHz, d$_6$-DMSO, TMS for Example No. C1 and 250 MHz, d$_6$-DMSO, TMS for Example No. C2/FIG. 1) show significant differences in the aromatic region: the H signals of the phenyl radical of Example No. C1 at about 7.1 ppm (3H) and 7.3 ppm (2H), the H signals of Example No. C2 at about 7.3 ppm (5H). This finding has been applied to the compounds of Examples 2 and 3 (FIG. 2) and to other derivatives of this type, and the indicated absolute and relative configurations were found in this way.

The compounds in Table 1 are prepared in analogy to the method in example 1, 2 and 3:

TABLE 1

| Ex No. | Isomer | A | G | L | M | X | a) m.p. (° C.) b) R$_f$ (solvent) | Spectra | Starting material from Ex. No. |
|---|---|---|---|---|---|---|---|---|---|
| 4 | / | H | Me | H | Me | H | | MS (FAB): 464 ([M + H]$^+$, 20%) | CXXII |
| 5 | 2 dia | H | Me | H | Me | Me | b) 0.28/0,33 (D) | | CXXIII |
| 6 | dia A | H | Me | H | Me | Me | b) 0.28 (D) | | CXXIII |
| 7 | dia B | H | Me | H | Me | Me | b) 0.33 (D) | | CXXIII |
| 8 | 2 dia | H | Me | H | Me | Et | b) 0.28/0,31 (D) | | CXXIV |
| 9 | dia A | H | Me | H | Me | Et | b) 0.28 (D) | | CXXIV |
| 10 | dia B | H | Me | H | Me | Et | b) 0.31 (D) | | CXXIV |

TABLE 1-continued

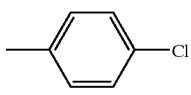

| Ex No. | Isomer | A | G | L | M | X | a) m.p. (° C.)<br>b) $R_f$ (solvent) | Spectra | Starting material from Ex. No. |
|---|---|---|---|---|---|---|---|---|---|
| 11 | 2 dia | H | Me | H | Me | nPr | b) 0.46/0,63 (D) | | CXXV |
| 12 | dia A | H | Me | H | Me | nPr | b) 0.63 (D) | | CXXV |
| 13 | dia B | H | Me | H | Me | nPr | b) 0.46 (D) | | CXXV |
| 14 | 2 dia | H | Me | H | Me | nBu | b) 0.44 (D) | | CXXVI |
| 15 | dia A | H | Me | H | Me | nBu | b) 0.44 (D) | | CXXVI |
| 16 | dia B | H | Me | H | Me | nBu | b) 0.44 (D) | | CXXVI |
| 17 | 2 dia | H | Me | H | Me | iBu | b) 0.42 (D) | | CXXVII |
| 18 | dia A | H | Me | H | Me | iBu | b) 0.42 (D) | | CXXVII |
| 19 | dia B | H | Me | H | Me | iBu | b) 0.42 (D) | | CXXVII |
| 20 | 2 dia | H | Me | H | Me | nPent | a) 149° C. | | CXXVIII |
| 21 | dia A | H | Me | H | Me | nPent | | MS (FAB) 533 ($M^+$, 100%) | CXXVIII |
| 22 | dia B | H | Me | H | Me | nPent | a) 140° C. | | CXXVIII |
| 23 | 2 dia | H | Me | H | Me | iPent | a) 174° C. | | CXXIX |
| 24 | dia A | H | Me | H | Me | iPent | a) 164° C. | | CXXIX |
| 25 | dia B | H | Me | H | Me | iPent | a) 204° C. | | CXXIX |
| 26 | 2 dia | H | Me | H | Me | —CH(Et)$_2$ | a) 110° C. | | CXXX |
| 27 | din A | H | Me | H | Me | —CH(Et)$_2$ | a) 112° C. | | CXXX |
| 28 | dia B | H | Me | H | Me | —CH(Et)$_2$ | a) 193° C. | | CXXX |
| 29 | 2 dia | H | Me | H | Me | nHex | b) 0.63/0,58 (D) | | CXXXI |
| 30 | dia A | H | Me | H | Me | nHex | b) 0.63 (D) | | CXXXI |
| 31 | dia B | H | Me | H | Me | nHex | b) 0.58 (D) | | CXXXI |
| 32 | 2 dia | H | Me | H | Me | —CH$_2$CH(Et)$_2$ | a) 179° C. | | CXXXII |
| 33 | dia A | H | Me | H | Me | —CH$_2$CH(Et)$_2$ | | MS (FAB) 547 ($M^+$, 100%) | CXXXII |
| 34 | dia B | H | Me | H | Me | —CH$_2$CH(Et)$_2$ | b) 181° C. | | CXXXII |
| 35 | 2 dia | H | Me | H | Me | cHex | b) 0.31 (E) | | CXXXIII |
| 36 | dia A | H | Me | H | Me | cHex | b) 0.31 (E) | | CXXXIII |
| 37 | dia B | H | Me | H | Me | cHex | b) 0.31 (E) | | CXXXIII |
| 38 | 2 dia | H | Me | H | Me | cHept | b) 0.42 (D) | | CXXXIV |
| 39 | dia A | H | Me | H | Me | cHept | b) 0.42 (D) | | CXXXIV |
| 40 | dia B | H | Me | H | Me | cHept | b) 0.42 (D) | | CXXXIV |
| 41 | 2 dia | H | Me | H | Me | cOct | b) 0.35/0.40 (D) | | CXXXV |
| 42 | dia A | H | Me | H | Me | cOct | b) 0.40 (D) | | CXXXV |
| 43 | dia B | H | Me | H | Me | cOct | b) 0.35 (D) | | CXXXV |
| 44 | 2 dia | H | Me | H | Me | —CH$_2$—cPent | b) 0.32 (D) | | CXXXVI |
| 45 | dia A | H | Me | H | Me | —CH$_2$—cPent | b) 0.32 (D) | | CXXXVI |
| 46 | dia B | H | Me | H | Me | —CH$_2$—cPent | b) 0.32 (D) | | CXXXVI |
| 47 | 2 dia | H | Me | H | Me | 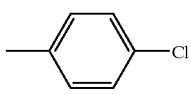 | a) 122° C. | | CIL |
| 48 | dia A | H | Me | H | Me | 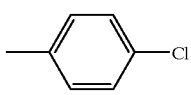 | a) 226° C. | | CIL |
| 49 | dia B | H | Me | H | Me | (4-Cl-C$_6$H$_4$) | a) 216° C. | | CIL |
| 50 | 2 dia | H | Me | H | Et | cPent | a) 202° C. | | CXXXVII |
| 51 | 2 dia | H | Et | H | Me | cPent | a) 172° C. | | CXXXVIII |
| 52 | 2 dia | H | Et | H | Et | cPent | a) 190° C. | | CXXXIX |
| 53 | 2 dia | H | Me | Me | Me | cPent | a) 215° C. | | CXL |

TABLE 1-continued

| Ex No. | Isomer | A | G | L | M | X | a) m.p. (° C.) b) R_f (solvent) | Spectra | Starting material from Ex. No. |
|---|---|---|---|---|---|---|---|---|---|
| 54 | dia A | H | Me | Me | Me | cPent | a) 197° C. | | CXL |
| 55 | dia B | H | Me | Me | Me | cPent | a) >230° C. | | CXL |
| 56 | 2 dia | H | Me | Et | Me | cPent | b) 0.13 (B) | | CXLV |
| 57 | 2 dia | H | Et | Me | Me | cPent | b) 0.33 (D) | | CXLVI |
| 58 | 2 dia | H | Me | Me | Et | cPent | b) 0.28 (D) | | CXLVII |
| 59 | 2 dia | 6-Cl | Me | H | Me | cPent | a) 160° C. | | CXLI |
| 60 | 2 dia | 7-Cl | Me | H | Me | cPent | a) 158° C. | | CXLII |
| 61 | 2 dia | 6-OMe | Me | H | Me | cPent | a) 144° C. | | CXLIII |
| 62 | 2 dia | 7-OMe | Me | H | Me | cPent | a) 155° C. | | CXLIV |

TABLE 2

| Ex No. | Isomer | A | G | L | M | X | a) m.p. (° C.) b) R_f (solvent) | Spectra | Starting material from Ex. No. |
|---|---|---|---|---|---|---|---|---|---|
| 63 | 2 dia | H | Me | H | Me | cPent | b) 0.23 (F) | | CXXI |
| 64 | dia A | H | Me | H | Me | cPent | b) 0.23 (F) | | CXXI |
| 65 | dia B | H | Me | H | Me | cPent | b) 0.23 (F) | | CXXI |
| 66 | dia A | H | Me | Me | Me | cPent | a) 198° C. | | CXL |
| 67 | dia B | H | Me | Me | Me | cPent | a) >230° C. | | CXL |

The compounds in Table 3 are prepared in analogy to the method in Example 1:

TABLE 3

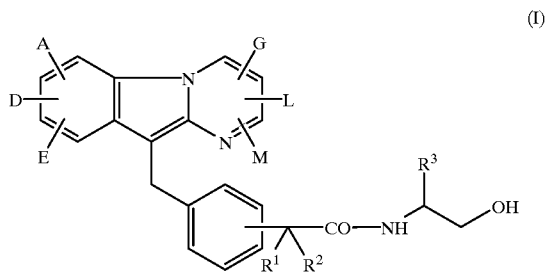

| Ex. No. | -X- | a) m.p. (° C.)<br>b) R$_f$ (solvent) | spectra | Starting material from Ex. No. |
|---|---|---|---|---|
| 68 | C(Me)$_2$ | b) 0,42 (F) | | CLVII |
| 69 | C(Et)$_2$ | a) 76° C. | | CLVIII |
| 70 | C(nPr)$_2$ | b) 0.26 (F) | | CLIX |
| 71 | C(NBu)$_2$ | b) 0.21 (F) | | CLX |
| 72 | cyclopentyl | a) 85° C. | | CLXI |
| 73 | cyclohexyl | a) 174° C. | | CLXII |
| 74 | cycloheptyl | a) 166° C. | | CLXIII |

We claim:

1. A pyrimido[1,2-a]indole compound of the formula (I):

(I)

in which

A, D, E, G, L and M are identical or different and represent hydrogen, halogen, trifluoromethyl, carboxyl, hydroxyl, straight-chain or branched alkoxy having 1 to 6 carbon atoms, straight-chain or branched alkoxycarbonyl having 2 to 6 carbon atoms, or straight-chain or branched alkyl having 1 to 6 carbon atoms, which alkyl is optionally substituted by hydroxyl or by straight-chain or branched alkoxy having 1 to 4 carbon atoms;

R$^1$ and R$^2$ are identical or different and represent hydrogen, cycloalkyl having 3 to 8 carbon atoms, or straight-chain or branched alkyl having 1 to 10 carbon atoms, which alkyl is optionally substituted by cycloalkyl with 3 to 6 carbon atoms, or R$^1$ and R$^2$ represent phenyl which is optionally substituted by halogen or trifluoromethyl; or R$^1$ and R$^2$ together with the carbon atom to which they are bonded form a 4- to 8-membered cycloalkyl ring; and R$^3$ represents phenyl which is optionally substituted 1 to 3 times, identically or differently, by nitro, carboxyl, halogen, cyano, straight-chain or branched alkenyl having 2 to 6 carbon atoms, alkoxycarbonyl having 2 to 6 carbon atoms, or straight-chain or branched alkyl having 1 to 6 carbon atoms, which alkyl is optionally substituted by hydroxyl, carboxyl, straight-chain or branched alkoxy having 1 to 6 carbon atoms, or straight-chain or branched alkoxycarbonyl having 2 to 6 carbon atoms, and/or said phenyl is optionally substituted by a group of the formula —OR$^4$ or —NR$^5$R$^6$;

in which

R$^4$ is hydrogen, straight-chain or branched alkyl having 1 to 6 carbon atoms, or straight-chain or branched alkenyl having 2 to 6 carbon atoms;

R$^5$ and R$^6$ are identical or different and denote phenyl, hydrogen, straight-chain or branched alkyl having 1 to 6 carbon atoms, or straight-chain or branched acyl having 1 to 8 carbon atoms, which acyl is optionally substituted by a group of the formula —NR$^7$R$^8$;

in which

R$^7$ and R$^8$ are identical or different and denote hydrogen or straight-chain or branched acyl having 1 to 8 carbon atoms;

optionally in the form of a purified stereoisomer thereof or a mixture of two or more stereoisomers thereof, or a salt of said compound, purified stereoisomer or stereoisomer mixture.

2. A pyrimido[1,2-a]indole compound of the formula (I) according to claim 1, in which A, D, E, G, L and M are identical or different and represent hydrogen, fluorine, chlorine, bromine, trifluoromethyl, carboxyl, hydroxyl, straight-chain or branched alkoxy having 1 to 4 carbon atoms, straight-chain or branched alkoxycarbonyl having 2 to 4 carbon atoms, or straight-chain or branched alkyl having 1 to 4 carbon atoms, which alkyl is optionally substituted by hydroxyl or by straight-chain or branched alkoxy having 1 to 3 carbon atoms;

$R^1$ and $R^2$ are identical or different and represent hydrogen, cyclopropyl, cyclobutyl, cyclopentyl, cyclohexyl, cycloheptyl, cyclooctyl, or straight-chain or branched alkyl having 1 to 8 carbon atoms, which alkyl is optionally substituted by cyclopropyl, cyclopentyl or cyclohexyl, or $R^1$ and $R^2$ represent phenyl which is optionally substituted by fluorine, chlorine or bromine; or $R^1$ and $R^2$ together with the carbon atom to which they are bonded form a 4- to to 7-membered cycloalkyl ring, and $R^3$ represents phenyl which is optionally substituted 1 to 3 times, identically or differently, by nitro, carboxyl, fluorine, chlorine, bromine, cyano, straight-chain or branched alkenyl having 2 to 4 carbon atoms, alkoxycarbonyl having 2 to 4 carbon atoms, or straight-chain or branched alkyl having 1 to 5 carbon atoms, which alkyl is optionally substituted by hydroxyl, carboxyl, straight-chain or branched alkoxy having 1 to 5 carbon atoms, or straight-chain or branched alkoxycarbonyl having 2 to 5 carbon atoms, and/or said phenyl is optionally substituted by a group of the formula —$OR^4$ or —$NR^5R^6$;

in which $R^4$ is hydrogen, straight-chain or branched alkyl having 1 to 4 carbon atoms, or straight-chain or branched alkenyl having 2 to 4 carbon atoms;

$R^5$ and $R^6$ are identical or different and denote phenyl, hydrogen, straight-chain or branched alkyl having 1 to 5 carbon atoms, or straight-chain or branched acyl having 1 to 6 carbon atoms, which acyl is optionally substituted by a group of the formula —$NR^7R^8$;

in which $R^7$ and $R^8$ are identical or different and denote hydrogen or straight-chain or branched acyl having 1 to 6 carbon atoms;

optionally in the form of a purified stereoisomer thereof, and a salt of said compound or purified stereoisomer.

3. A pyrimido[1,2-a]indole compound of the formula (I) according to claim 1, in which A, D, E, G, L and M are identical or different and represent hydrogen, fluorine, chlorine, bromine, trifluoromethyl, carboxyl, hydroxyl, straight-chain or branched alkoxy having 1 to 3 carbon atoms, straight-chain or branched alkoxycarbonyl having 2 to 3 carbon atoms, or straight-chain or branched alkyl having 1 to 3;

$R^1$ and $R^2$ are identical or different and represent hydrogen, cyclopropyl, cyclobutyl, cyclopentyl, cyclohexyl, cycloheptyl, cyclooctyl, or straight-chain or branched alkyl having 1 to 6 carbon atoms, which alkyl is optionally substituted by cyclopropyl, cyclopentyl or cyclohexyl, or $R^1$ and $R^2$ represent phenyl which is optionally substituted by fluorine, chlorine or bromine; and $R^3$ represents phenyl;

optionally in the form of a purified stereoisomer thereof, and a salt of said compound or purified stereoisomer.

4. A process for preparing a pyrimido[1,2-a]indole compound of the formula (I) according to claim 1, said process comprising amidating a racemic or enantiomerically pure carboxylic acid or activated derivative thereof of the formula (II):

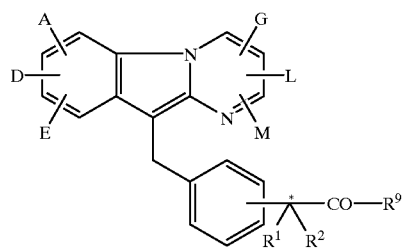

in which $R^9$ represents hydroxyl or an activating radical;

with a phenylglycinol of the formula (III):

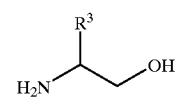

in an inert solvent, and optionally in the presence of a base and/or an ancillary substance.

5. A process according to claim 4, wherein $R^9$ represents chlorine.

6. A composition for treating atherosclerosis comprising a pharmaceutically acceptable carrier and an antiatherosclerotic effective amount of a pyrimido[1,2-a]indole compound of the formula (I), purified stereoisomer thereof, or salt of said compound or purified stereoisomer according to claim 1.

7. A method of treating atherosclerosis in a patient in need thereof comprising administering to said patient an antiatherosclerotic effective amount of a pyrimido[1,2-a]indole compound of the formula (I), purified stereoisomer thereof, or salt of said compound or purified stereoisomer according to claim 1.

8. A carboxylic acid of the formula (II):

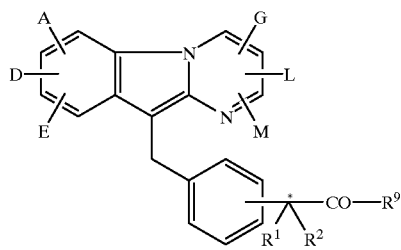
(II)

in which
  A, D, E, G, L and M are identical or different and represent hydrogen, halogen, trifluoromethyl, carboxyl, hydroxyl, straight-chain or branched alkoxy having 1 to 6 carbon atoms, straight-chain or branched alkoxycarbonyl having 2 to 6 carbon atoms, or straight-chain or branched alkyl having 1 to 6 carbon atoms, which alkyl is optionally substituted by hydroxyl or by straight-chain or branched alkoxy having 1 to 4 carbon atoms;
  $R^1$ and $R^2$ are identical or different and represent hydrogen, cycloalkyl having 3 to 8 carbon atoms, or straight-chain or branched alkyl having 1 to 10 carbon atoms, which alkyl is optionally substituted by cycloalkyl with 3 to 6 carbon atoms, or $R^1$ and $R^2$ represent phenyl which is optionally substituted by halogen or trifluoromethyl; or
  $R^1$ and $R^2$ together with the carbon atom to which they are bonded form a 4- to 8-membered cycloalkyl ring; and
  $R^9$ represents hydroxyl or an activating radical;
or a salt thereof.

9. A carboxylic acid of the formula (II) according to claim 8, wherein $R^9$ represents chlorine.

10. A process for preparing a carboxylic acid of the formula (II) according to claim 8, said process comprising reacting a compound of the formula (IV):

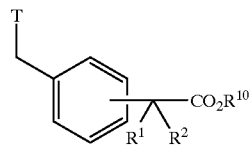
(IV)

in which
  T represents a leaving group; and
  $R^{10}$ represents alkyl having 1 to 4 carbon atoms;
with a compound of the formula (V):

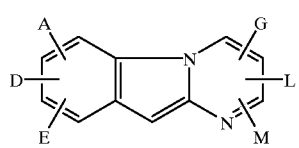
(V)

in an inert solvent, optionally in the presence of a base, to yield a compound of the formula (VI):

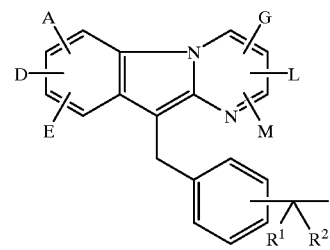
(VI)

and the compound of the formula (VI) is hydrolyzed to the compound of formula (II).

11. A process according to claim 10, wherein T represents a leaving group selected from the group consisting of chlorine, bromine, iodine, tosylate and mesylate.

12. A process according to claim 11, wherein T represents bromine.

13. A compound according to claim 1, which has the formula

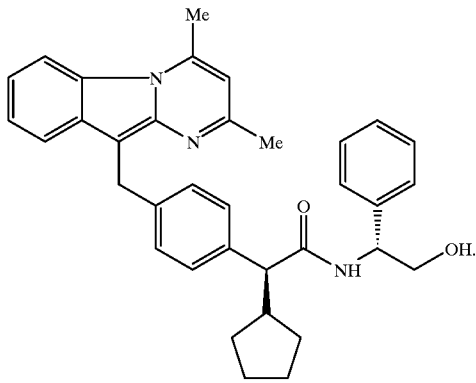

14. A compound according to claim 1, which has the formula

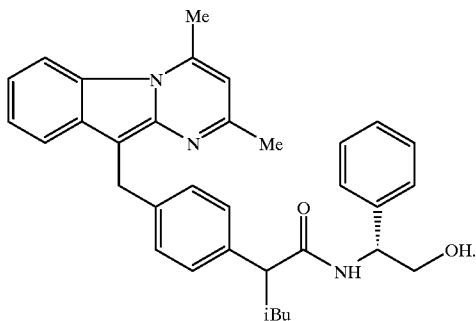

15. A compound according to claim 1, which has the formula

16. A compound according to claim 1, which has the formula
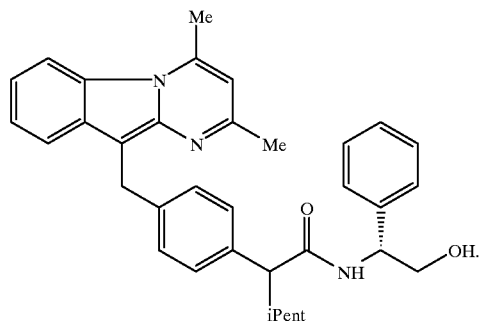
17. A compound according to claim 1, which has the formula
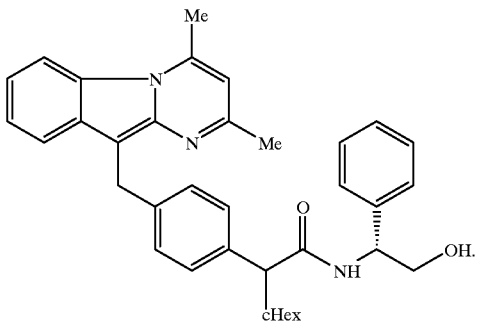
18. A compound according to claim 1, which has the formula
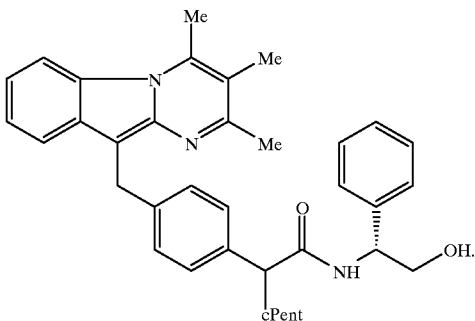
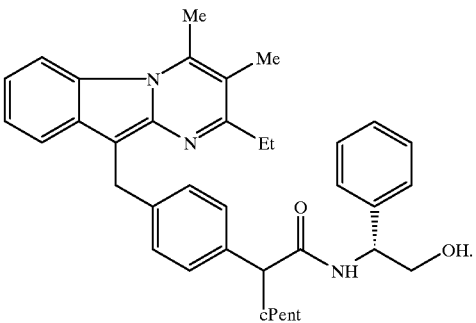
* * * * *